(12) United States Patent
Hong et al.

(10) Patent No.: US 10,307,210 B2
(45) Date of Patent: Jun. 4, 2019

(54) OPTICAL TRACKING SYSTEM AND TRACKING METHOD USING THE SAME

(71) Applicants: KOH YOUNG TECHNOLOGY INC., Seoul (KR); KYUNGPOOK NATIONAL UNIVERSITY INDUSTRY ACADEMIC COOPERATION FOUNDATION, Daegu (KR)

(72) Inventors: Jong-Kyu Hong, Gwangju-si (KR); Hyun-Ki Lee, Daegu (KR); Min-Young Kim, Daegu (KR); You-Seong Chae, Daegu (KR)

(73) Assignees: KOH YOUNG TECHNOLOGY INC., Seoul (KR); KYUNGPOOK NATIONAL UNIVERSITY INDUSTRY ACADEMIC COOPERATION FOUNDATION, Daegu (KR)

( * ) Notice: Subject to any disclaimer, the term of this patent is extended or adjusted under 35 U.S.C. 154(b) by 87 days.

(21) Appl. No.: 14/391,447

(22) PCT Filed: Apr. 29, 2014

(86) PCT No.: PCT/KR2014/003782
§ 371 (c)(1),
(2) Date: Oct. 9, 2014

(87) PCT Pub. No.: WO2014/178610
PCT Pub. Date: Nov. 6, 2014

(65) Prior Publication Data
US 2016/0287341 A1 Oct. 6, 2016

(30) Foreign Application Priority Data

Apr. 30, 2013 (KR) .................. 10-2013-0047984
May 28, 2013 (KR) .................. 10-2013-0060034
May 28, 2013 (KR) .................. 10-2013-0060035

(51) Int. Cl.
*A61B 5/00* (2006.01)
*A61B 34/20* (2016.01)
*A61B 90/00* (2016.01)

(52) U.S. Cl.
CPC .............. *A61B 34/20* (2016.02); *A61B 90/39* (2016.02); *A61B 2034/2055* (2016.02);
(Continued)

(58) Field of Classification Search
CPC .... A61B 2090/3937; A61B 2090/3945; A61B 2090/3983; A61B 2034/2065
See application file for complete search history.

(56) References Cited

U.S. PATENT DOCUMENTS

2006/0293557 A1 12/2006 Chuanggui et al.
2007/0183041 A1 8/2007 McCloy et al.
(Continued)

FOREIGN PATENT DOCUMENTS

CN 101170961 4/2008
JP 63-45504 2/1988
(Continued)

OTHER PUBLICATIONS

International Search Report for International Application No. PCT/KR2014/003782, dated Aug. 22, 2014.
(Continued)

Primary Examiner — Rajeev P Siripurapu
(74) Attorney, Agent, or Firm — Kile Park Reed & Houtteman PLLC

(57) ABSTRACT

An optical tracking system and a method using the same capable of detecting an exact spatial position and a direction of a target regardless of the distance from the target to be calculated is disclosed. The optical tracking system and a
(Continued)

method using the same according to an embodiment of the present invention has an effect of expanding an available area by detecting an exact spatial position and a direction of a target regardless of the distance from the target to be calculated, as well as, a system downsizing is also achieved by significantly reducing size of the marker unit compared with conventional system.

11 Claims, 32 Drawing Sheets

(52) U.S. Cl.
CPC .................. *A61B 2034/2065* (2016.02); *A61B 2090/3945* (2016.02); *A61B 2090/3983* (2016.02)

(56) References Cited

U.S. PATENT DOCUMENTS

2008/0317281 A1 12/2008 Goldbach
2011/0254922 A1 10/2011 Schaerer et al.
2012/0078236 A1* 3/2012 Schoepp ................ A61B 5/061
606/1

FOREIGN PATENT DOCUMENTS

| JP | 11-83426 | 3/1999 |
|---|---|---|
| JP | 2007-130398 | 5/2007 |
| JP | 2010-190793 | 9/2010 |
| JP | 2011-136005 | 7/2011 |
| KR | 10-2010-0098055 | 9/2010 |
| KR | 10-2012-0035021 | 4/2012 |

OTHER PUBLICATIONS

Written Opinion for International Application No. PCT/KR2014/003782, dated Aug. 22, 2014.
Japanese Office Action with English translation for Japanese Application No. 2017-253282, dated Dec. 18, 2018.

* cited by examiner

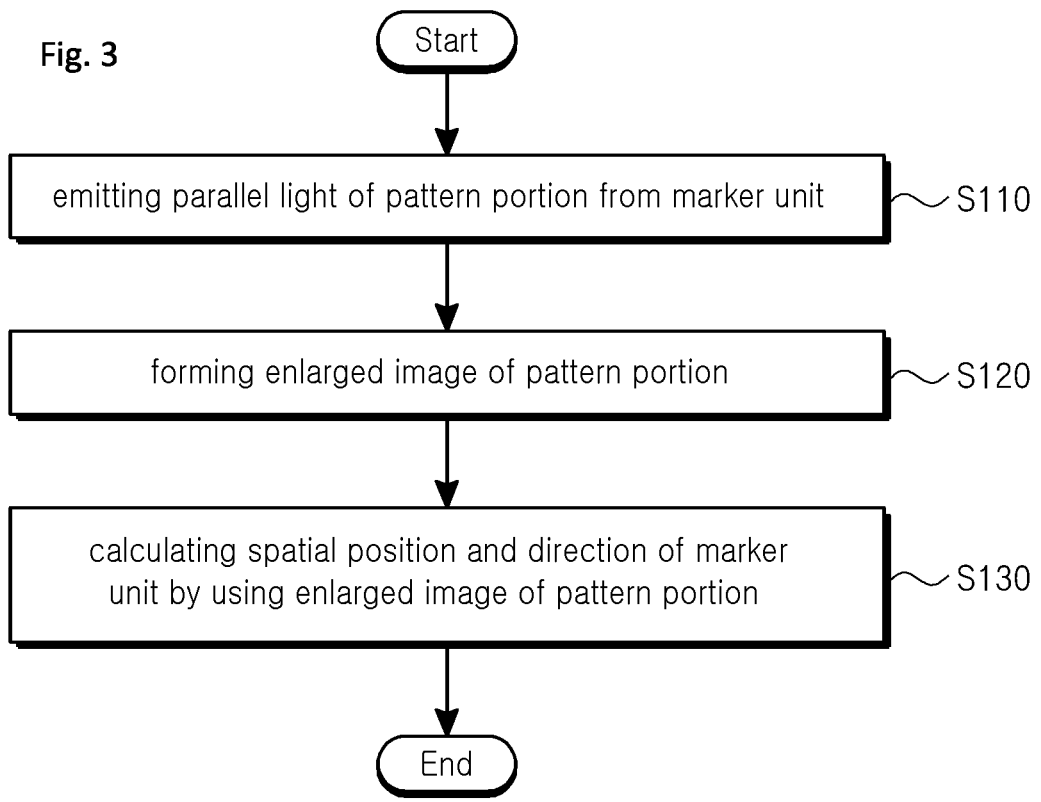
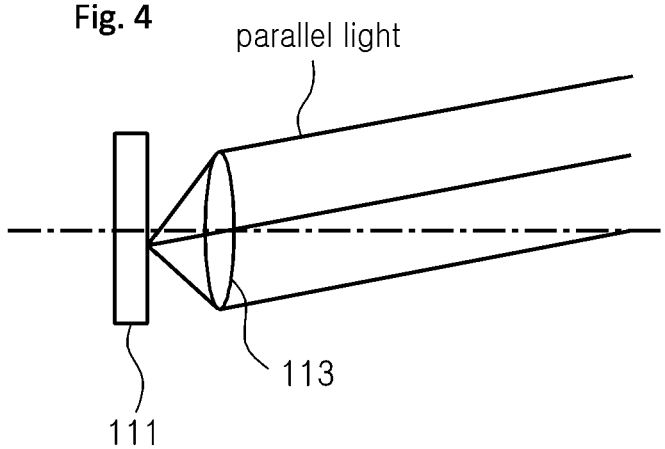

OPTICAL TRACKING SYSTEM AND TRACKING METHOD USING THE SAME

TECHNICAL FIELD

Exemplary embodiments of the present invention relate to an optical tracking system and tracking method using the same. More particularly, exemplary embodiments of the present invention relate to a tracking system and tracking method using the same for surgery capable of detecting a spatial and direction information of a target by tracking coordinates of markers attached on the target, in which the target are markers attached on a patient or surgical instrument.

BACKGROUND ART

Recently, a robot surgery have been studied and introduced to reduce the pain of patients and to recover faster in an endoscopic surgery or an otolaryngology surgery (ENT surgery).

In such a robot surgery, in order to minimize a risk of the surgery and to operate the surgery more precisely, a navigation system is used to navigate to an exact lesion of a patient by tracking and detecting a spatial position and direction of a target such as lesion portion or surgical instrument.

The navigation system described above includes a tracking system which is capable of tracking and detecting a spatial position and direction of a target such as lesion or surgical instrument.

The tracking system described above includes a plurality of markers attached on a lesion or a surgical instrument, a first and second image forming units to form images of lights provided by the markers, and a processor calculating a 3-dimensional coordinates of the markers which are coupled to the first and second image forming units and calculating a spatial position and a direction of the target by comparing pre-stored information of straight lines connecting the markers adjacent to each other and angle information formed by a pair of straight lines adjacent to each other with the 3-dimensional coordinates of the markers.

A conventional tracking system and method as described above uses diameters of a circle of the markers formed on the image forming unit to calculate separated distances between the markers through the processor. But, a border of circle of the marker is opaque by a distortion of a lens of the image forming unit, it is difficult to calculate exactly the diameters of the circle of the markers, as well as, exact positions of the markers since a change of diameters of the markers are slight and hard to distinguish.

DISCLOSURE

Technical Problem

Therefore, the technical problem of the present invention is to provide an optical tracking system and method using the same capable of detecting an exact spatial position and a direction of a target regardless of the distance from the target to be calculated.

Technical Solution

In one embodiment of the present invention, an optical tracking system includes at least one marker unit which is attached on a target and emits a parallel light to form an enlarged image of a pattern portion, in which the pattern portion is included inside the marker unit, an image forming unit which receives the parallel light of the pattern portion provided by the marker unit and forms the enlarged image of the pattern portion, and a processor which calculates a spatial position and a direction of the marker unit by using the enlarged image of the pattern portion formed on the image forming unit.

In one embodiment, the marker unit may include at least one pattern portion on which plurality of patterns are formed, at least one light source irradiating light toward the pattern portion, and at least first lens portion passing a parallel light to the image forming unit in which the light is emitted from the light source and has passed or is reflected by the pattern portion.

Herein, it may be preferable to arrange the pattern portion at a focal length of the first lens portion.

Meanwhile, the first lens portion may be an objective lens.

In one embodiment, the light source may be arranged inside the marker unit.

Alternatively, the light source may be arranged outside the marker unit.

Herein, the light source may be an LED (Light Emitting Diode).

In one embodiment, the image forming unit may be a camera which receives the parallel light of the pattern portion through the lens portion which is provided by the marker unit and forms an enlarged image of the pattern portion on a sensor portion.

Meanwhile, the processor may calculate a spatial position of the marker unit by using a position and a size change of the enlarged image of pattern portion formed on the image forming unit, and a direction of the marker unit by using positions of the pattern portion and a size change of the pattern portion for each area of the enlarged image of the pattern portion.

In one embodiment, the processor may calculate a spatial position of the marker unit by comparing a position and size of the enlarged image of the pattern portion formed on the image forming unit with a pre-stored reference position and a pre-stored reference size of the image of the pattern portion, and calculate a direction of the marker unit by comparing a position of the pattern and a pattern size for each area of the enlarged image of the pattern portion with a pre-stored reference pattern position and pre-stored pattern size for each area of the enlarged pattern portion.

Meanwhile, the marker unit may reflect and release light, which is irradiated from at least one light source, in a parallel light form through a ball lens in which a pattern portion is formed on a surface. Herein, the pattern portion may be wholly or partially formed on the surface of the ball lens.

In another embodiment, the marker unit may pass and release light, which is irradiated from at least one light source and is reflected by or have passed the pattern portion, in parallel light form through a fisheye lens.

The pattern portion may be arranged at a focal length of the fisheye lens.

Also, the light source may be arranged outside the marker unit such that the light is reflected by the pattern portion and passes the fisheye lens. Alternatively, the light source may be arranged in the inside the marker unit such that the light irradiated from the light sources passes through the pattern portion and passes the fisheye lens.

In another embodiment, the marker unit may pass and release the light, which is emitted from the at least one light source, and is reflected by the pattern portion or have passed the pattern portion, in parallel light form through an objective lens, and releases the parallel light through a prism to have different angle of views.

The pattern portion may be arranged at a focal length of the objective lens.

Or, the light source may be arranged outside the marker unit to such that the light is reflected by the pattern portion and passes the objective lens. Alternatively, the light source may be arranged inside the marker unit such that the light irradiated from the light source passes through the pattern portion and passes the objective lens.

In another embodiment, the marker unit may reflect and release the light, which is irradiated from at least one light source, in parallel light form through a mirror portion on which a pattern portion is formed.

The marker unit may further include a first lens arranged at an interval from the mirror portion to change and release the parallel light, which is reflected by the mirror portion, once more in a parallel light form.

Also, the marker unit may further include an aperture installed on the mirror portion to adjust an angle of view and a resolution of the enlarged image of the pattern portion formed on the image forming unit by adjusting a light quantity of the light flowed in to the mirror portion.

Meanwhile, the mirror portion is a mirror with a spherical or non-spherical shape.

Next, a method of tracking using an optical tracking system according to an embodiment of the present invention includes steps of emitting a parallel light from a marker unit attached on a target to enlarge an image of a pattern portion, receiving the parallel light provided by the marker unit and forming an image of the enlarged image of the pattern portion on an image forming unit, and calculating a spatial position and a direction of the marker unit through a processor by using the enlarged image of the pattern portion formed on the image forming unit.

In one embodiment, calculating a spatial position and a direction of the marker unit may include steps of calculating a direction of the marker unit by calculating a rotated angle of the marker unit through the processor by using the enlarged image of the pattern portion formed on the image forming unit, and calculating a spatial position of the marker through the processor by using the enlarged image of the pattern portion formed on the image forming unit and the rotated angle of the marker unit.

Herein, calculating the direction of the marker unit may include steps of measuring a position and a size change of the pattern portion for each area of the enlarged image of the pattern portion formed on the image forming unit through the processor, and calculating the rotated angle of the marker unit by comparing a position of a reference pattern portion and a size of the reference pattern portion, which are pre-stored in the processor, with the position and the size change of the pattern portion for each area of the enlarged image of the pattern portion formed on the image forming unit.

And, calculating the spatial position of the marker unit may include steps of measuring a position and a size of the enlarged pattern portion formed on the image forming unit through the processor, and calculating the spatial position of the marker unit by comparing a reference position and a reference size of the image of the pattern portion which are pre-stored in the processor.

In one embodiment, the marker unit may reflect and release the light, which is irradiated from at least one light source, in parallel light form through a ball lens in which a pattern portion is formed on a surface of the ball lens.

In another embodiment, the marker unit may pass and release the light, which is irradiated from at least one light source and is reflected by or has passed the pattern portion, in parallel light form through a fisheye lens.

In another embodiment, the marker unit may pass and release the light, which is emitted from the at least one light source and is reflected by or have passed the pattern portion, in parallel light form through an objective lens, and releases the parallel light through a prism to have different angle of views.

In another embodiment, the marker unit may reflect and release the light, which is irradiated from at least one light source, in parallel light form through a mirror portion on which a pattern portion is formed.

Advantageous Effects

Thus, an optical tracking system and a method using the same according to an embodiment of the present invention calculates a spatial position of a marker unit by using an enlarged image of a pattern portion which is formed on an image forming unit by emitting a parallel light from the marker unit to a pattern portion. In other words, the spatial position and the direction of the target to be calculated are calculated without reduction of accuracy by enlarging the image of the pattern portion and forming the enlarged image on the image forming unit, and therefore, an accuracy of the position of the marker unit is not dependent on a resolving power.

Therefore, an optical tracking system and a method using the same according to an embodiment of the present invention has an effect of expanding an available area by detecting an exact spatial position and a direction of a target regardless of the distance from the target to be calculated, as well as, a system downsizing is also achieved compared with conventional system.

DESCRIPTION OF DRAWINGS

FIG. 3 is a flow chart explaining a method of tracking a target using an optical tracking system according to a first embodiment;

FIG. 4 is a drawing explaining a process of emitting light from a marker unit;

MODE FOR INVENTION

Figure 1:
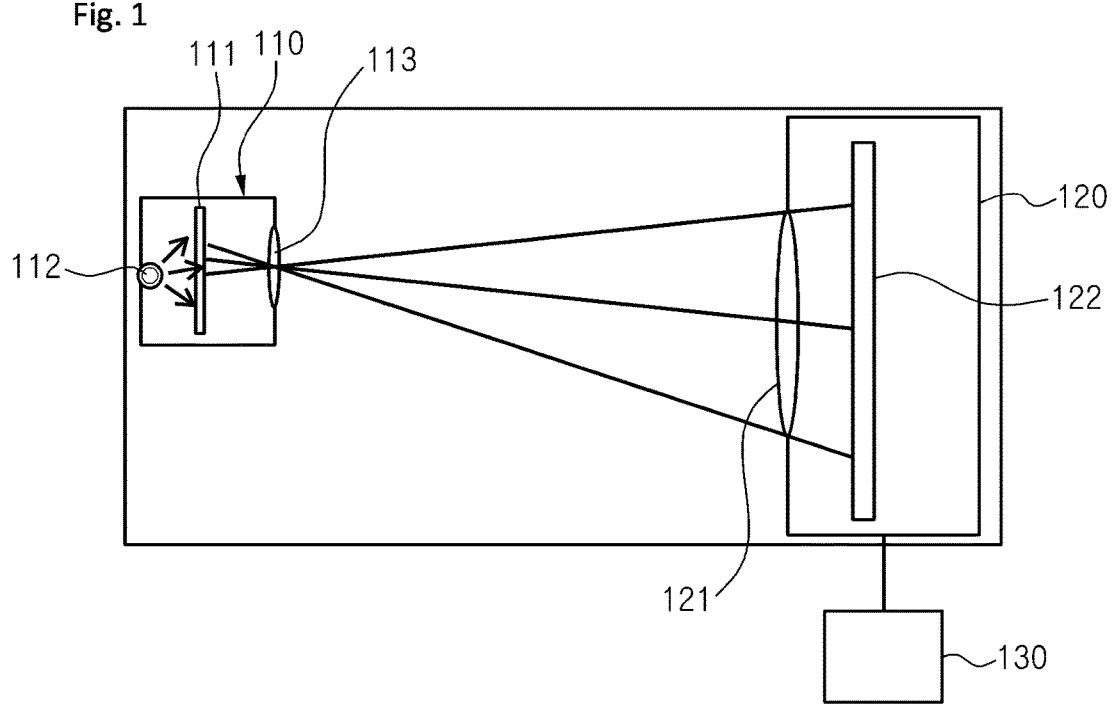
FIG. 1 is a schematic diagram of a tracking system according to a first embodiment of the present invention.

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that, although the terms first, second, third etc. may be used herein to describe various elements, components, regions, layers and/or sections, these elements, components, and/or sections should not be limited by these terms. These terms are only used to distinguish one element, component, region, layer or section from another region, layer or section. Thus, a first element, component, or section discussed below could be termed a second element, component, or section without departing from the teachings of the present invention.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, with reference to the drawings, preferred embodiments of the present invention will be described in detail.

An optical tracking system and method using the same according to an embodiment of the present invention attaches at least one marker on a target such as a lesion or a surgical instrument, receives a parallel light emitted from the marker through the image forming unit and forms an enlarged image of a pattern portion on an image forming unit, and calculates a spatial position and a direction of the target through a processor by using the enlarged image of the pattern portion. The detailed description is explained with reference to figures.

First Embodiment

Figure 2:
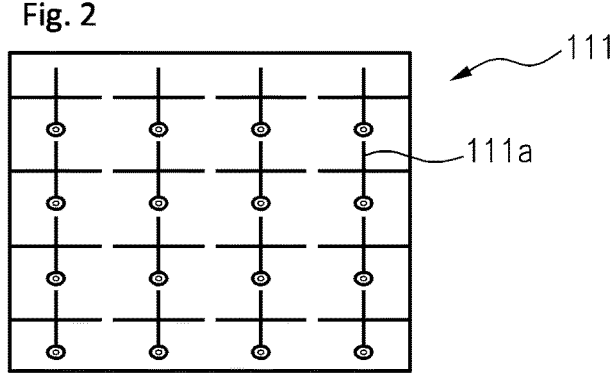
FIG. 2 is an example drawing of a pattern portion of a marker unit.

FIG. 1 is a schematic diagram of a tracking system according to a first embodiment of the present invention, and FIG. 2 is an example drawing of a pattern portion of a marker unit.

Referring to FIGS. 1-2, a tracking system according to a first embodiment of the present invention includes a marker unit 110, an image forming unit 120, and a processor 130.

The marker unit 110 attached on a target and emits a parallel light to form an enlarged image of a pattern portion 111 which is included inside the marker unit 110.

For example, the marker unit 110 may include a pattern portion 111, a light source 112, and a first lens portion 113.

The pattern portion is formed by plurality of pattern portions 111a in a regular shape with an interval. For example, the pattern portion 111 may be formed to pass light except for an area in which pattern portions 111a are formed. Alternatively, the pattern portions 111a may be formed to pass light an area in which the pattern portions 111a are formed. Alternatively, the pattern portion 111 may be formed to reflect light emitted from the light source 112. Herein, the pattern portion 111 may be arranged at a focal length of the first lens portion 113 which will be described below.

The light source 112 irradiates light toward the pattern portion 111. For example, the light source 112 is arranged inside the marker unit 110 to be positioned in a rear portion of the pattern portion 111. As described above, when the light source 112 is arranged in the rear of the pattern portion 111, the light emitted from the light source 112 passes through the pattern portion 111 and is incident on the image forming unit 120 described below. Alternatively, the light source 112 may be arranged outside the marker unit 110. When the light source 112 is arranged outside the marker unit 110, the light irradiated from the light source 112 is reflected by the pattern portion 111 and is incident on the image forming unit 120 described below. Herein, the light source 112 may be an LED (Light Emitting Diode).

The first lens portion 113 is arranged in front of the pattern portion 111 to emit a parallel light toward the image forming unit 120 in which the light is irradiated from the light source 112 and has passed or reflected by the pattern portion 111. For example, the first lens portion 113 may be an objective lens to enlarge an image of the pattern portion 111 and forming an enlarged image on the image forming unit 120.

The image forming unit 120 receives the parallel light of the pattern portion 111 which is provided by the marker unit 110 and forms an enlarged image of the pattern portion 111. Herein, the image forming unit 120 may be a camera receiving the parallel light of the pattern portion 111 which is provided by the marker unit 110 and forming the enlarged image of the pattern portion 111 on an image sensor 122.

The processor 130 is connected to the image forming unit 120, and calculates a spatial position and a direction of the marker unit 120 by using the enlarged image of the pattern portion 111 formed on the image forming unit 120. Herein, the processor 130 may calculate a spatial position of the marker unit 110 by using a position and a size change of the enlarged image of the pattern portion 111 formed on the image forming unit 120. Also, the processor 130 may calculate a direction of the marker unit 110 by using a size change of the pattern portion 111a and a position of the pattern portion for each area of the enlarged pattern portion 111.

Referring to FIGS. 1-7d, a detailed process of calculating a spatial position and a direction of a target using an optical tracking system according to the first embodiment is explained below.

Figure 5:
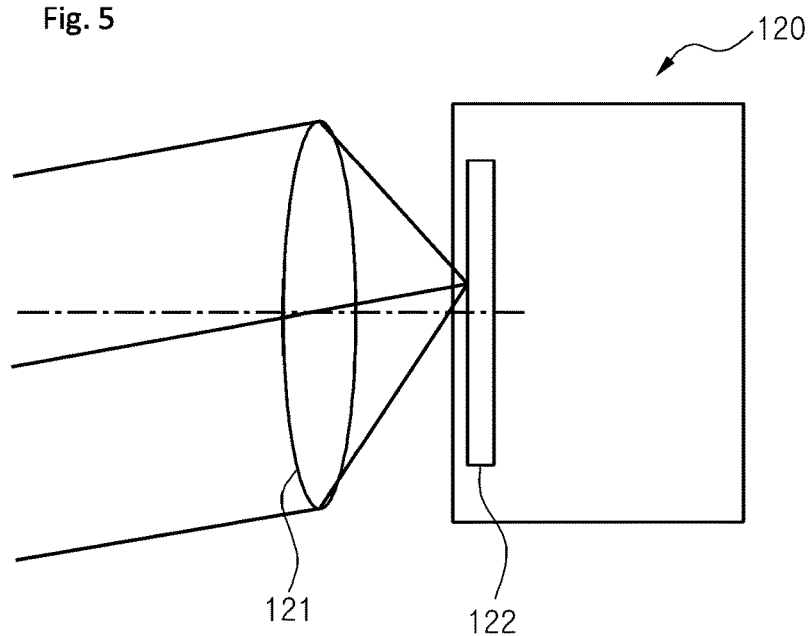
FIG. 5 is a drawing explaining a process of a parallel light being incident on an image forming unit.
Figure 6:
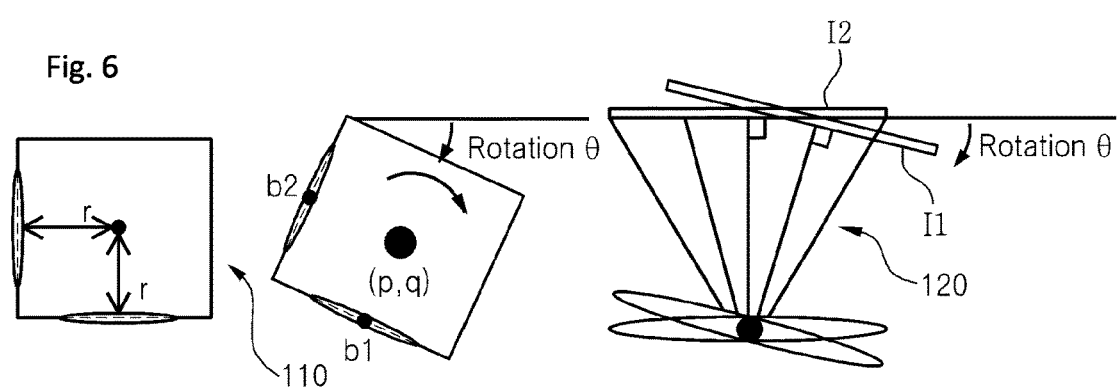
FIG. 6 is a flow chart explaining a method of calculating a direction of a target using an optical tracking system of the first embodiment.
Figure 7A:
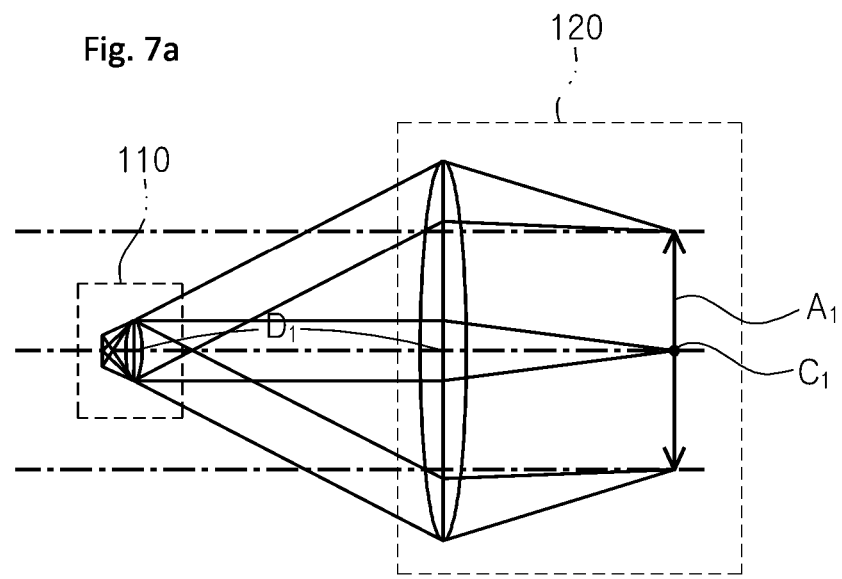
FIGS. 7a-7d are drawings explaining a method of calculating a spatial position of a target using an optical tracking system according to a first embodiment.
Figure 7B:
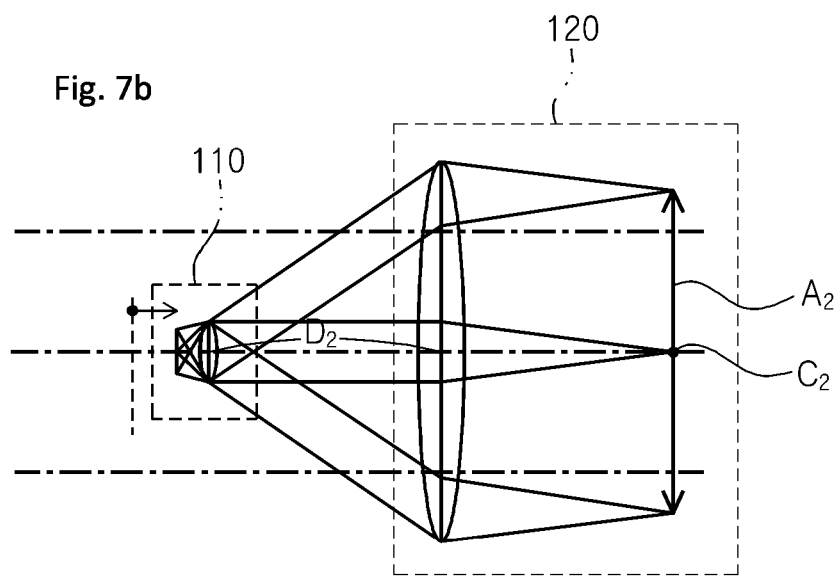
Figure 7C:
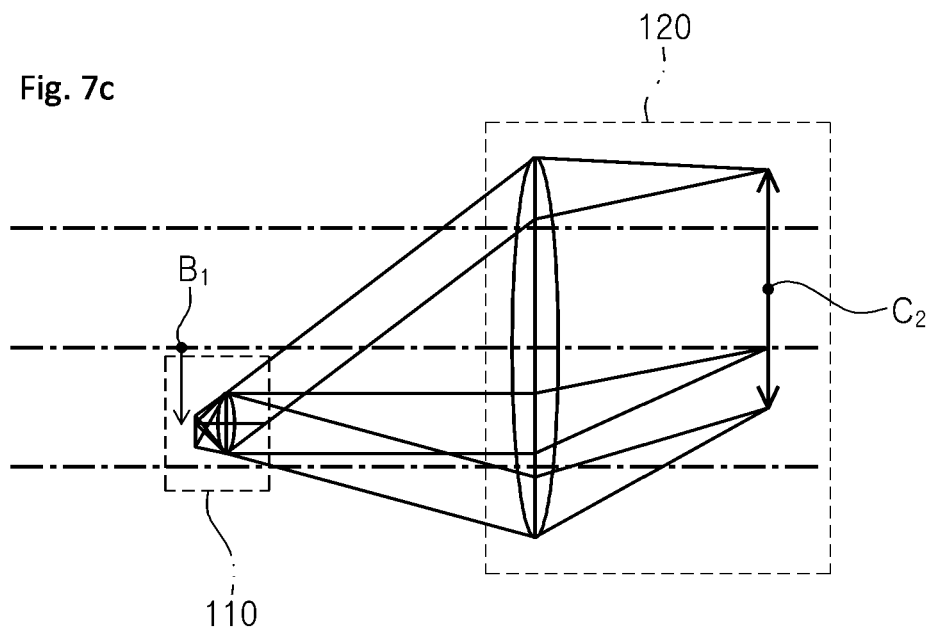
Figure 7D:
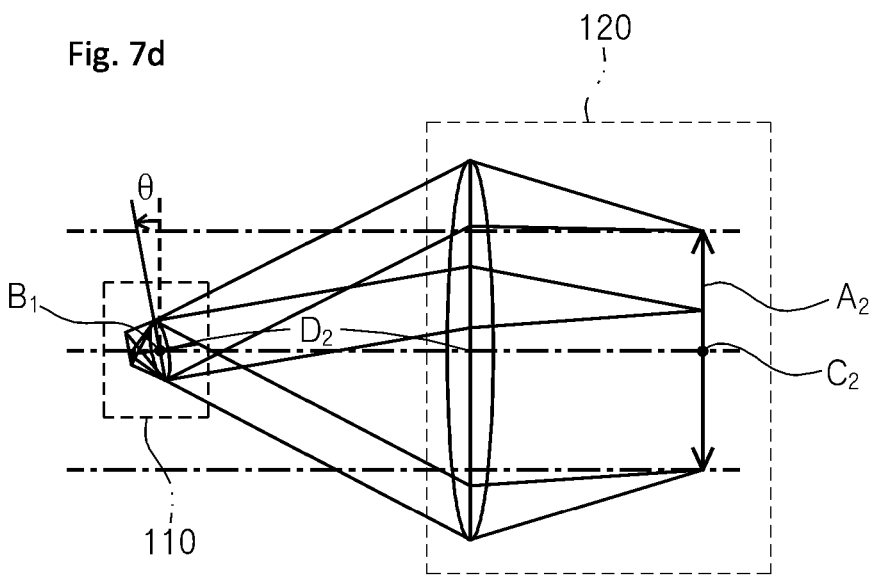
Figure 8:
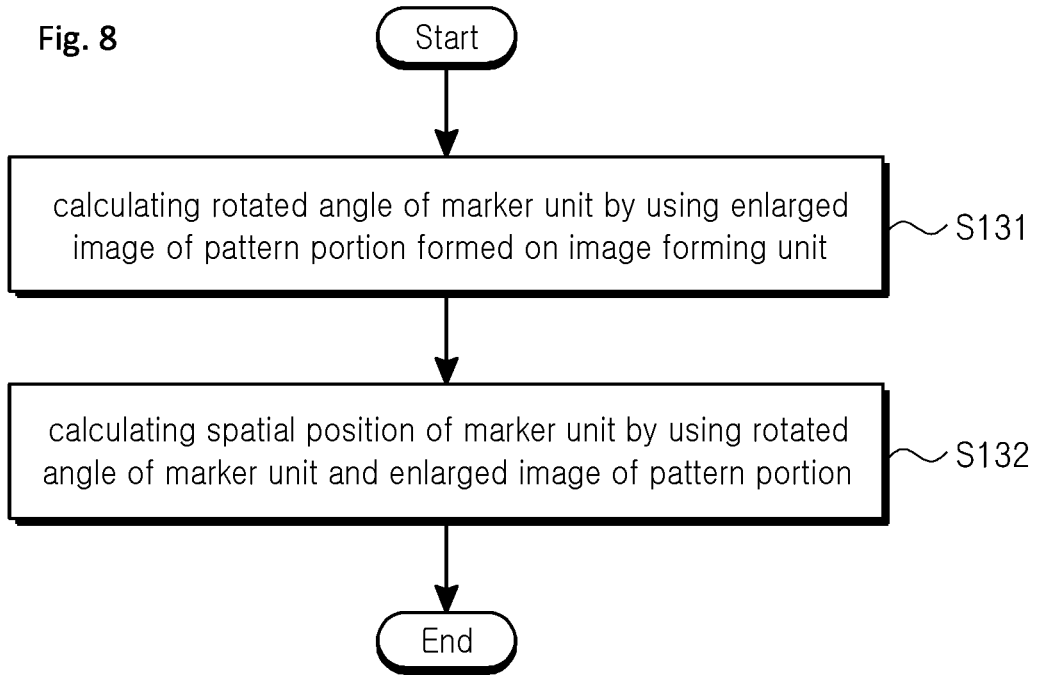
FIG. 8 is a flow chart explaining a process of calculating of a spatial position and a direction of a marker unit.
Figure 9:
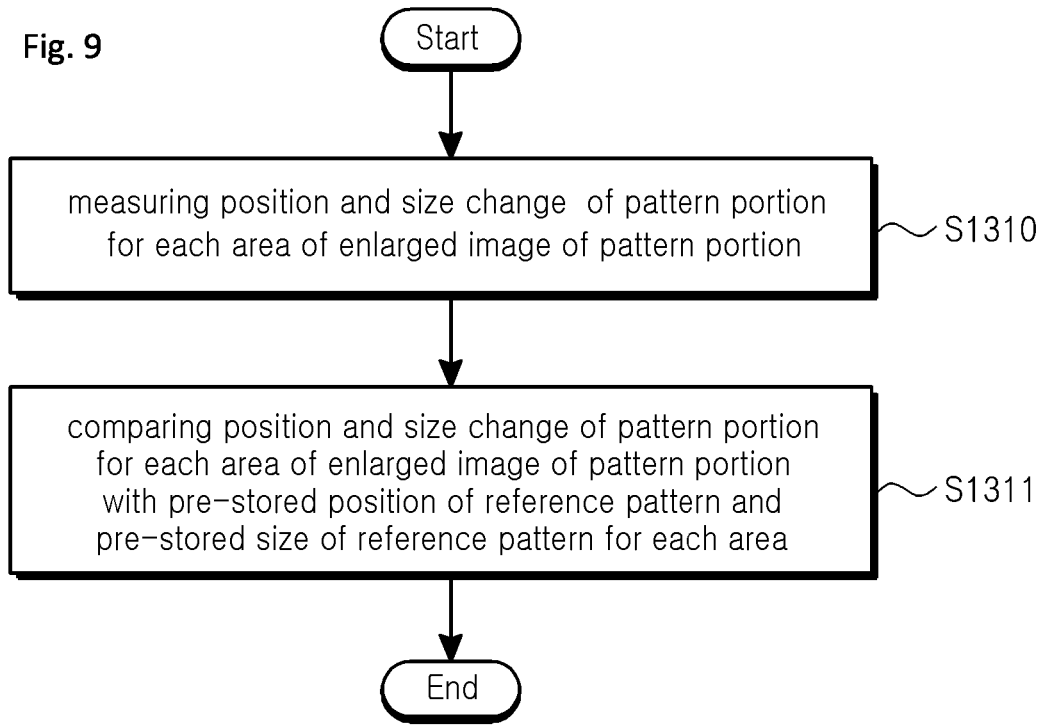
FIG. 9 is a flow chart explaining a process of calculating of a direction of a marker unit.
Figure 10:
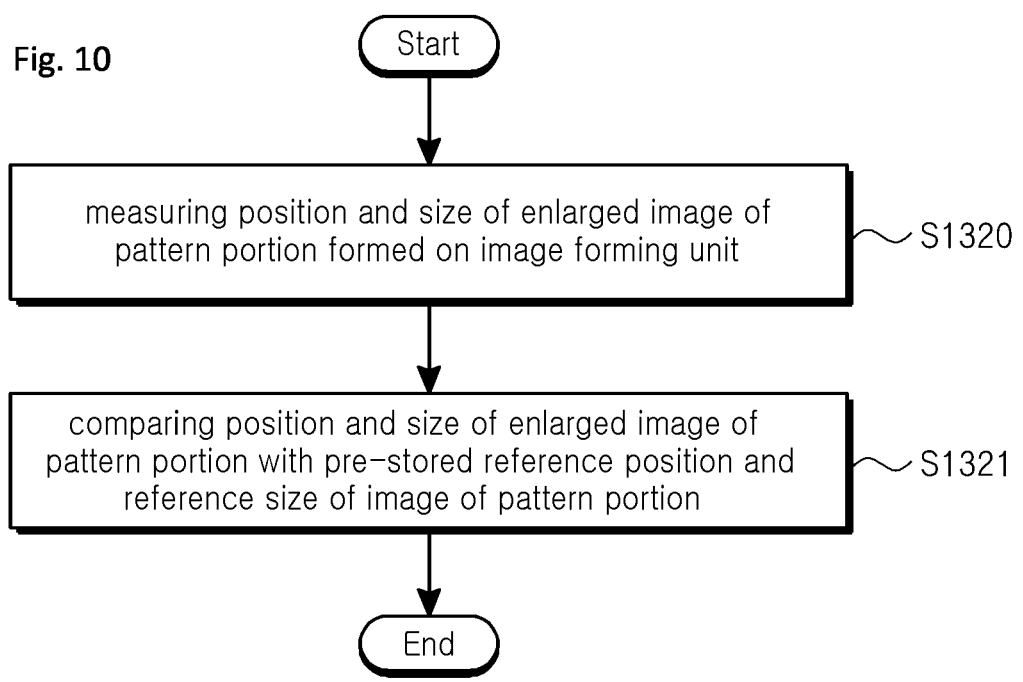
FIG. 10 is a flow chart explaining a process of calculating a spatial position of a marker unit.

FIG. 3 is a flow chart explaining a method of tracking a target using an optical tracking system according to a first embodiment, FIG. 4 is a drawing explaining a process of emitting light from a marker unit, FIG. 5 is a drawing explaining a process of a parallel light being incident on an image forming unit, FIG. 6 is a flow chart explaining a method of calculating a direction of a target using an optical tracking system of the first embodiment, FIGS. 7a-7d are drawings explaining a method of calculating a spatial position of a target using an optical tracking system according to a first embodiment, FIG. 8 is a flow chart explaining a process of calculating of a spatial position and a direction of a marker unit, FIG. 9 is a flow chart explaining a process of calculating of a direction of a marker unit, and FIG. 10 is a flow chart explaining a process of calculating of a spatial position of a marker unit.

Referring to FIGS. 1-7d, in order to track a target using an optical tracking system according to the first embodiment of the present invention, first, a parallel light is emitted from the marker unit 120 through the pattern portion 111 to form an enlarged image of the pattern portion 111 (S110).

Explaining in detail the process of emitting a parallel light of a pattern portion 111, first, a light is irradiated toward the pattern portion 111 by operating a light source 112 such that a partial of the light passes through or is reflected by the pattern portion 111. The light, which passes through or is reflected by the pattern portion 111, is emitted in a parallel light by passing a first lens portion 113 formed by an objective lens as shown in FIG. 4.

The parallel light of the pattern portion 111, which has passed the first lens portion 113 emitted from a marker unit 110, is incident on an image forming unit to form an enlarged image of the pattern portion 111 (S120).

Explaining in detail the process of forming the enlarged image of the pattern portion 111, the parallel light of the pattern portion, which has passed the first lens portion 113 and provided by the marker unit 110, passes a lens portion 121 of the image forming unit 120 as shown in FIG. 5.

When the enlarged image of the pattern portion is formed on the image forming unit 120, a spatial position and a direction of the marker unit 110 are calculated through a processor 130 by using the enlarged image of the pattern portion 111 (S130).

A detailed explanation of calculating the spatial position and the direction of the marker unit 120 is explained with reference to FIG. 8.

FIG. 8 is a flow chart explaining a process of calculating of a spatial position a direction of a marker unit.

Referring to FIG. 8, in order to calculate a spatial position and a direction of the marker unit 110, a direction of the marker unit 110 is calculated by calculating a rotated angle of the marker unit 110 through the processor 130 by using the enlarged image of the pattern portion 111 (S131).

When the rotated angle of the marker unit 110 is calculated, the processor calculates a spatial position of the marker unit 110 by using the rotated angle of the marker unit 110 and the enlarged image of the pattern portion 111 (S132).

Herein, a spatial position and a direction of the image forming unit 120 is pre-stored in the processor 130.

A detailed explanation of calculating the direction of the marker unit 120 is explained with reference to FIGS. 6 and 9.

FIG. 9 is a flow chart explaining a process of calculating of a direction of a marker unit.

Referring to FIG. 9, in order to calculate the direction of the marker unit 110, first, a position of the pattern portion 111a and a size change of the pattern portion 111a for each area of the enlarged image of the pattern portion 111 formed on the image forming unit 120 are measured by the processor 130 (S1310).

When the position of the pattern portion 111a and the size change of the pattern portion 111a for each area are calculated, the direction of the marker unit 110 is calculated through the processor 130 by calculating a rotated angle of the marker unit 110. The rotated angle of the marker unit is calculated by comparing a reference position of the pattern portion 111a and a reference size change of the pattern portion 111*a* for each area of the enlarged pattern image of the pattern portion, which are pre-stored in the processor 130, with the position of the pattern portion 111*a* and the size change of the pattern portion 111*a* for each area of the enlarged image of the pattern portion 111 formed on the image forming unit 120 (S1311).

In other words, as shown in FIG. 6, the position and the size of the pattern portions 111*a* of the enlarged image $I_1$ of the pattern portion 111 formed on the image forming unit 120 are changed as the marker unit 110 is rotated, and the processor 130 calculates the direction of the marker unit 110 by calculating the rotated angle of the marker unit 110 by comparing the position and the size change of the pattern portion 111*a* for each area of the enlarged image $I_1$ of the pattern portion 111 formed on the image forming unit 120 with the reference position of the pattern portion 111*a* and reference size change of the pattern portion 111*a* for each area of the enlarged pattern image of the pattern portion, which are pre-stored in the processor 130.

Next, a detailed explanation of calculating the spatial position of the marker unit 110 (S132) is explained with reference to FIGS. 7*a*-7*d*, and 10.

FIG. 10 is a flow chart explaining a process of calculating a spatial position of a marker unit.

Referring to FIG. 10, in order to calculate a spatial position of the marker unit 110, a position and a size of the enlarged image of the pattern portion 111 formed on the image forming unit 120 are measured by the processor 130 (S1320).

After measuring the position and the size of the enlarged image of the pattern portion 111, a spatial position of the marker unit 110 portion is calculated by the processor 130 by comparing a reference position and a size of the image of the pattern portion 111 with the position and the size of the enlarged image of the pattern (S1321).

FIG. 7*a* shows the reference position and the size of an image of the pattern portion 111 formed on the image forming unit 120 when the marker is positioned at a pre-stored position, which is stored in the processor 130, and as shown in FIG. 7*b*, when a distance D2 between the marker unit 110 and the image forming unit 120 is shorter than a reference distance D1, then, a size A2 of the enlarged image of the pattern portion 111 formed on the image forming unit 120 is bigger than a reference size A1 of the image of the pattern portion 111 which is pre-stored in the processor 130. Therefore, the spatial position of the marker unit 110 is calculated by comparing the reference size A1 of the image of the pattern portion 111 with the size A2 of the enlarged image of the pattern portion formed on the image forming unit 120.

Meanwhile, although it is not shown in the figure, when the distance D2 between the marker unit 110 and the image forming unit 120 is longer than the reference distance D1, then, the size A2 of the enlarged image of the pattern portion 111 formed on the image forming unit 120 is smaller than the reference size A1 of the image of the pattern portion 111 which is pre-stored in the processor 130.

And, when the marker unit is positioned below a reference position B1 as shown in FIG. 7*b* FIG. 7*c*, the enlarged image of the pattern image of the pattern portion III is formed on the image forming unit 120 positioning above a reference position C1 (Refer to FIG. 7*a*) of the image of the pattern portion 111 which is pre-stored in the processor 130. Therefore, the spatial position of the marker unit 110 is calculated through the processor 130 by comparing the reference position C1 of the image of the pattern portion 111 with a position C2 of the enlarged image of the pattern portion 111 formed on the image forming unit 120.

Meanwhile, although it is not shown in the figure, when the marker unit 110 is positioned at the reference position B1, the enlarged image of the pattern portion is formed on the image forming unit 120 positioning below the reference position C1 of the image of the pattern portion 111 which is pre-stored in the processor 130.

And, when the distance D2 between the marker unit 110 and the image forming unit 120 is different to the reference distance D1 and the marker unit 110 is not positioned at the reference position B1, the spatial position of the marker unit 110 is calculated by comparing the position C2 and the size A2 of the enlarged image formed on the image forming unit 120 with the reference position C1 and the reference size A1 of the image of the pattern portion 111 which is pre-stored in the processor 130.

Meanwhile, as shown in FIG. 7*d*, when the distance D2 between the marker unit 110 and the image forming unit 120 is identical to the reference distance D1, the marker unit 110 is positioned at the reference position B1 and the direction of the maker unit 110 is changed as θ, the calculated size A2 and position C2 of the enlarged image of the pattern portion 111 formed on the image forming unit 120 are identical to the reference position C1 and the reference size A1 of the image of the pattern portion 111 which is pre-stored in the processor 130. Therefore, the direction of the marker unit 111 is calculated by calculating the rotated angle of the marker unit 111 by comparing the position for each pattern portion 111*a* and the size change of the pattern portion 111*a* of the enlarged image $I_1$ of the pattern portion 111 with the reference position for each pattern portion 111*a* and the reference size of the pattern portion 111 of the image $I_2$ of the pattern portion 111 which are pre-stored in the processor 130.

Second Embodiment

An optical tracking system according to an embodiment of the present invention is substantially the same as the optical tracking system of the first embodiment except for arranging two image forming units, a detailed explanation of other elements except for an arrangement of the image forming unit is omitted.

Figure 11:
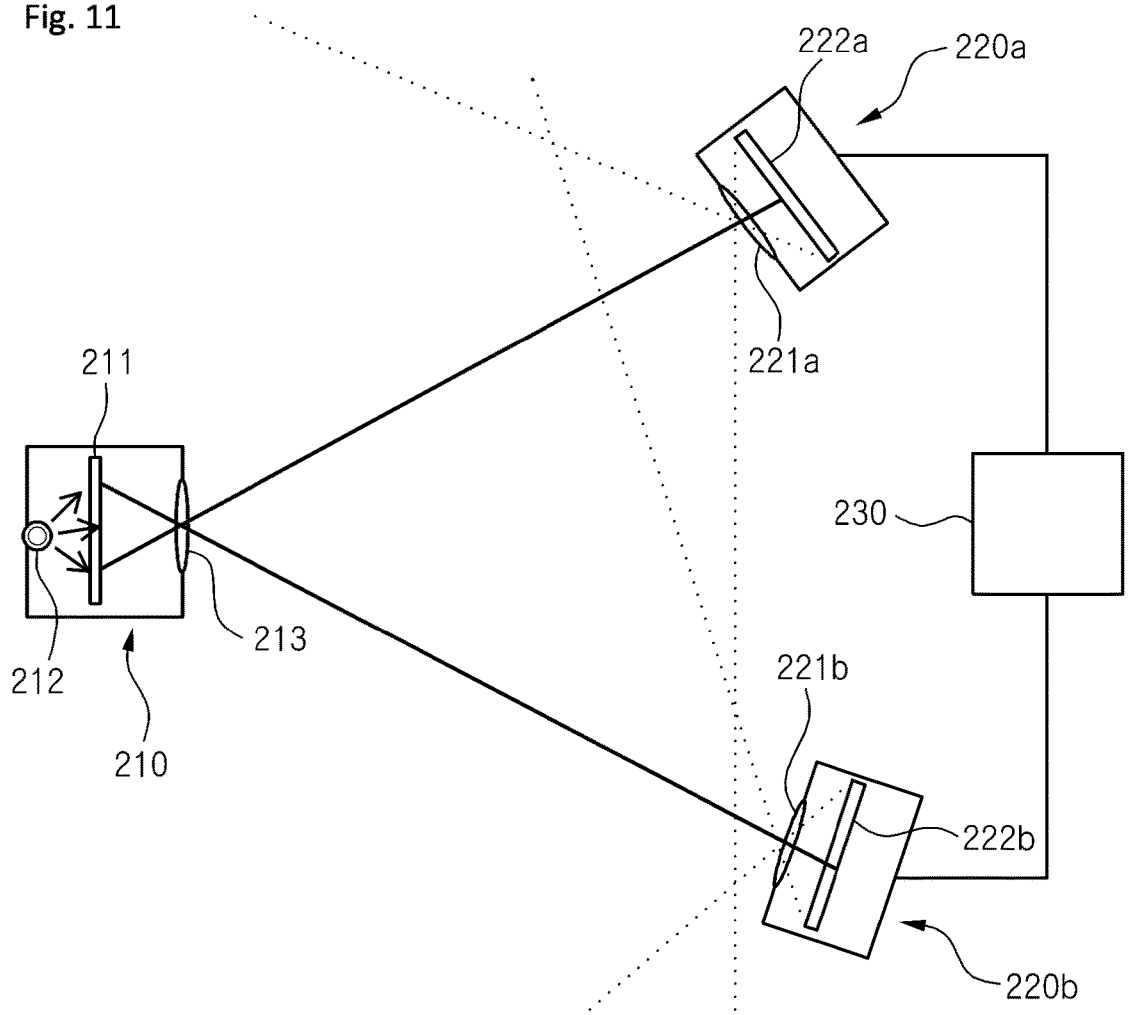
FIG. 11 is a schematic diagram of a tracking system according to a second embodiment of the present invention.

FIG. 11 is a schematic diagram of a tracking system according to a second embodiment of the present invention.

Referring to FIG. 11, an optical tracking system according to an embodiment of the present invention includes a maker unit 210, first and second image forming units 220*a* and 220*b*, and a processor 230.

The first and second image forming units 220*a* and 220*b* are arranged at an interval with the marker unit 210 as the center to receive a parallel light of the pattern portion 211 emitted from the marker unit 210 and form enlarged images of a pattern portion 211 which are different to each other. Herein, it may be preferable to arrange the first and second image forming units 220*a* and 220*b* in a Y-axis as shown in FIG. 11.

The optical tracking system according to an embodiment of the present invention forms two enlarged images of the pattern portion 111 by the first and second image forming units 220*a* and 220*b*, calculates two spatial position coordinates of the marker unit 210 by the processor 230, and therefore, calculates more precisely a spatial position and a direction of the marker unit 210 than the optical tracking system of the first embodiment.

A detailed explanation of calculating a spatial position and a direction of a marker unit using the optical tracking system according to an embodiment of the present invention is described in below with reference to FIGS. 11 and 12.

Figure 12:
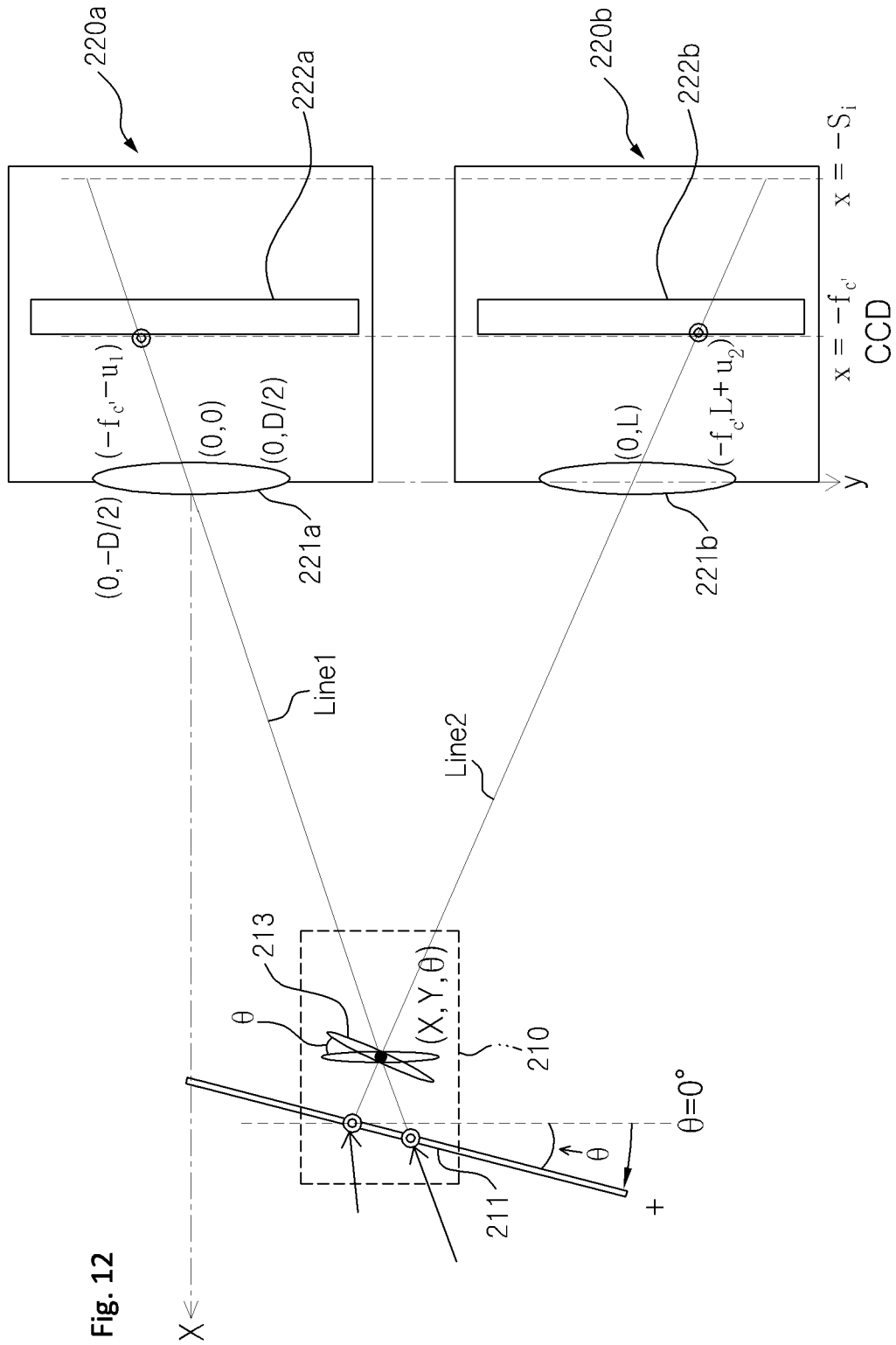
FIG. 12 is a drawing explaining a process of calculating a spatial position of a maker unit according to a second embodiment of the present invention.

FIG. 12 is a drawing explaining a process of calculating a spatial position of a maker unit according to a second embodiment of the present invention.

As shown in FIG. 12, a coordinate of a first lens portion 213 of a marker unit 210 is defined as X, Y, and the coordinate of the first lens portion 213 may be represented as a Formula 1

$$X = f_c L/u_1 + u_2$$

$$Y = u_1 L/u_1 + u_2 \qquad \text{[Formula 1]}$$

Herein, $f_c$ is a coordinate of an X-axis of an enlarged pattern portion 211 formed on a first and second image forming units 220a and 220b, L is a coordinate of an Y-axis of a lens portion 221b of the second image forming unit 220b, $u_1$ is a coordinate of an Y-axis of central coordinate of the enlarged pattern portion 211 formed on the first image forming unit 220a, and $u_2$ is a coordinate of an Y-axis of central coordinate of the enlarged pattern portion 211 formed on the second image forming unit 220a.

As shown in FIG. 12, when the first lens portion 213 of the marker unit 210 is fixed and rotated as θ, real coordinates $(X_1,Y_1)$ $(X_2,Y_2)$ of the pattern portion 211 is represented as a Formula 2.

$$(X_1, Y_1) = (\cos θf_b - \sin θu_1' + X, \sin θf_b + \cos θu_1' + Y)$$

$$(X_2, Y_2) = (\cos θf_b - \sin θu_2' + X, \sin θf_b + \cos θu_2' + Y) \qquad \text{[Formula 2]}$$

Herein, the $f_b$ is a focus length of the first lens portion 213 of the marker unit 210, and θ is rotated value of the marker unit 210.

And, a central coordinate of the enlarged pattern portion 211 formed on the first image forming unit 220a is defines as $X_3,Y_3$, and a central coordinate of the enlarged pattern portion 211 formed on the second image forming unit 220b is defines as $X_4,Y_4$, as shown in FIG. 12, it is confirmed that a central coordinate of the enlarged pattern portion 211 formed on the first image forming unit 220a $(X_3, Y_3)$, a central coordinate of the lens portion 221a of the first image forming unit 220a (0,0), a central coordinate of the first lens 213 of the marker unit 210 (X,Y), a real coordinate of the pattern portion 211 identified in the first image forming unit 220a $(X_1,Y_1)$ are placed on Line1, and a central coordinate of the enlarged pattern portion 211 formed on the second image forming unit 220b $(X_4,Y_4)$, a central coordinate of the lens portion 221b of the second image forming unit 220b (0,L), a central coordinate of the first lens 213 of the marker unit 210 (X,Y), a real coordinate of the pattern portion 211 identified in the second image forming unit 220a $(X_2,Y_2)$ are placed on Line2. Herein, $(X_3, Y_3) = (-f_c', -u_1)$, $(X_4, Y_4) = (-f_c', L+u_2)$, and $(X_1,Y_1)$ and $(X_2,Y_2)$ may be represented as Formula 2.

As described above, each coordinate of Line1 and Line2 may be represented using a Table 1.

TABLE 1

| | Real coordinate of the pattern portion (1) | Coordinate of the first lens portion (2) | Coordinate of the lens portion of the image forming unit (3) | Coordinate of the enlarged pattern portion (4) |
|---|---|---|---|---|
| Line 1 | $X_1, Y_1$ | X, Y | 0, 0 | $-f_c', -u_1$ |
| Line 2 | $X_2, Y_2$ | X, Y | 0, L | $-f_c', L + u_2$ |

Table 1 is an arranged table of coordinates which are placed on Line1 and Line2, generating two equations using the three coordinates (1), (2), and (3), and the difference between the two equations may be represented as Formula 3 with reference to the Table 1.

$$\cos θX(u_2'-u_1')+\sin θY(u_2'-u_1')+L(\cos θf_b - \sin θu_2')=0 \qquad \text{[Formula 3]}$$

Also, generating two equations using the three coordinates (1), (2), and (4) of the Line1 and Line2, and the difference between the two equations may be represented as Formula 4.

$$\sin θY(u_2'-u_1')+\cos θf_b(u_1+u_2)-\sin θ(u_1'u_1-u_2'u_2)+ r_1 X(u_2'-u_1')+\cos θf_c(u_2'-u_1')+L(\cos θf_b - \sin θu_2')=0 \qquad \text{[Formula 4]}$$

Also, generating two equations using the three coordinates (1), (3), and (4) of the Line1 and Line2, and the difference between the two equations may be represented as Formulas 5 and 6.

$$u_1 X + f_c Y + \cos θ(u_1' f_c - u_1 f_b) + \sin θ(u_1'u_1 + f_c f_b) = 0 \qquad \text{[Formula 5]}$$

$$u_2 X + f_c Y + \cos θ(u_2 f_b + u_2' + u_2' f_c) + \sin θ(f_b f_c - u_2'u_2) - Lf_c = 0 \qquad \text{[Formula 6]}$$

And tan θ is solved by substituting the Formula 3 to the Formula 4 and dividing into cos θ, and tan θ may be represented as Formula 7.

$$\tan θ = \sin θ/\cos θ = [-f_b(u_2-u_1)-f_c(u_2'-u_1')]/u_1'u_1 - u_2'u_2 \qquad \text{[Formula 7]}$$

Meanwhile, the θ value is known in the Formulas 5 and 6, the only parameters X,Y may be calculated by solving simultaneous equations constituted by the Formulas 5 and 6, and the coordinate (X,Y) of the first lens portion 213 of the marker unit 210 may be represented as Formula 8.

$$X = \{[(u_1+u_2)f_b-(u_1'-u_2')f_c]\cos θ-(u_1'u_1-u_2'u_2)\sin θ - Lf_c\}/(u_1-u_2)$$

$$Y = \{[(u_1'u_2-u_2'u_1)f_c - 2u_1u_2 f_b]\cos θ + [(u_1'+u_2')u_1 u_2 - (u_1+u_2)f_b f_c]\sin θ + Lf_c u_1\}/[(u_1-u_2)f_c] \qquad \text{[Formula 8]}$$

Third Embodiment

An optical tracking system according to an embodiment of the present invention is substantially the same as the optical tracking system of the first embodiment except for some elements, detailed explanations of other elements except for a marker unit is omitted.

Figure 13:
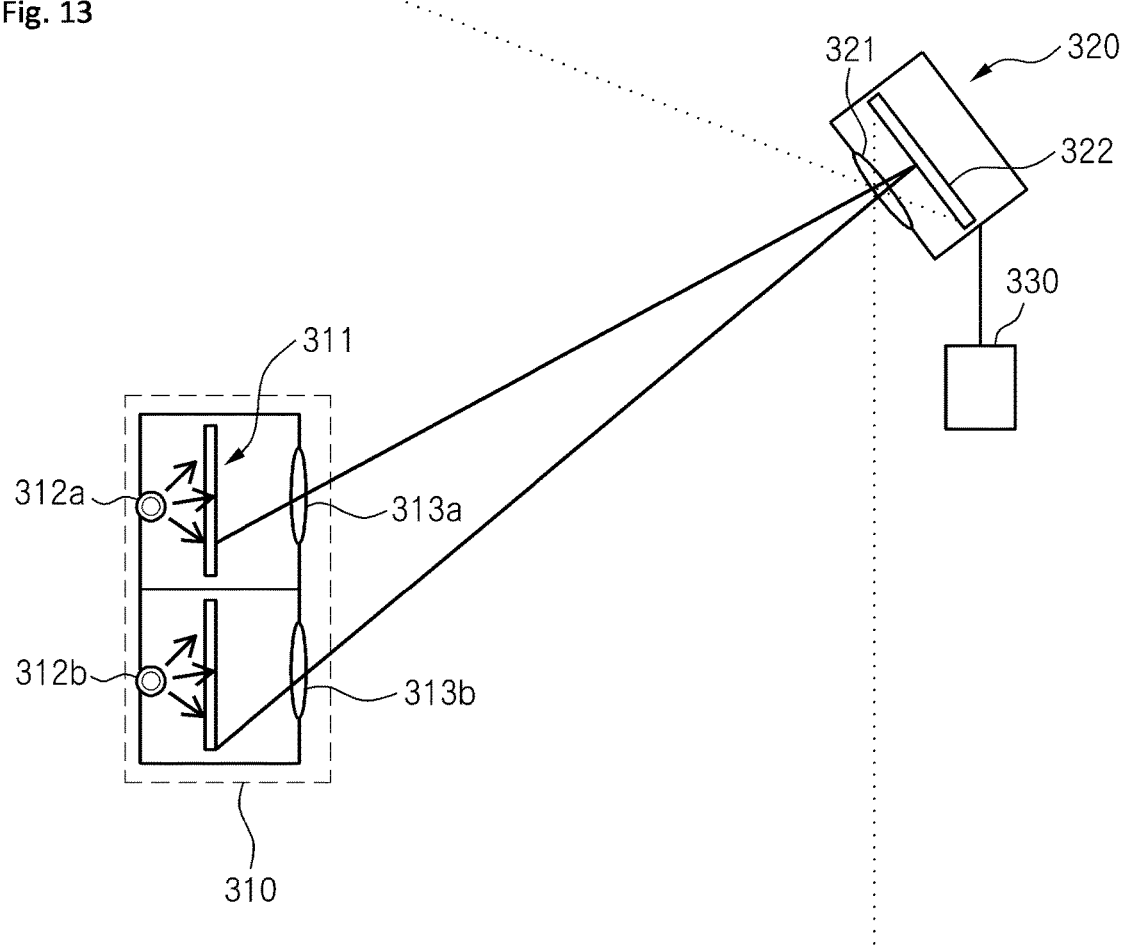
FIG. 13 is a schematic diagram of an optical tracking system according to a third embodiment of the present invention.

FIG. 13 is a schematic diagram of an optical tracking system according to a third embodiment of the present invention.

Referring to FIG. 13, an optical tracking system according to an embodiment of the present invention includes one marker unit 310, a first image forming unit 320, and a processor 330.

The marker unit 310 may include a pattern portion 311, first and second light sources 312a and 312b, and first and second lens portions 313a and 313b.

The pattern portion 311 is formed by plurality of pattern portions (not shown) with an interval. Herein, two pattern portions 311 may be formed which are corresponding to the first and second lens portions 313a and 313b as shown in FIG. 13, or, as well as one pattern portion 311 may be formed as shown FIG. 14, which will be described later.

The first and second light sources 312a and 312b are arranged on rear of the pattern portion 311 at an interval to irradiate lights toward the pattern portion 311.

The first and second lens portions 312a and 312b are formed in front of the pattern portion 311 at an interval to release the lights irradiated from the first and second light sources toward the pattern portion 311 in parallel light form.

A process of calculating a direction of the marker unit 310 according to an embodiment of the present invention is omitted as it is the same as the system of the first embodiment, and a process of calculating a spatial position of the marker unit 310 will be described with reference to FIG. 14.

Figure 14:
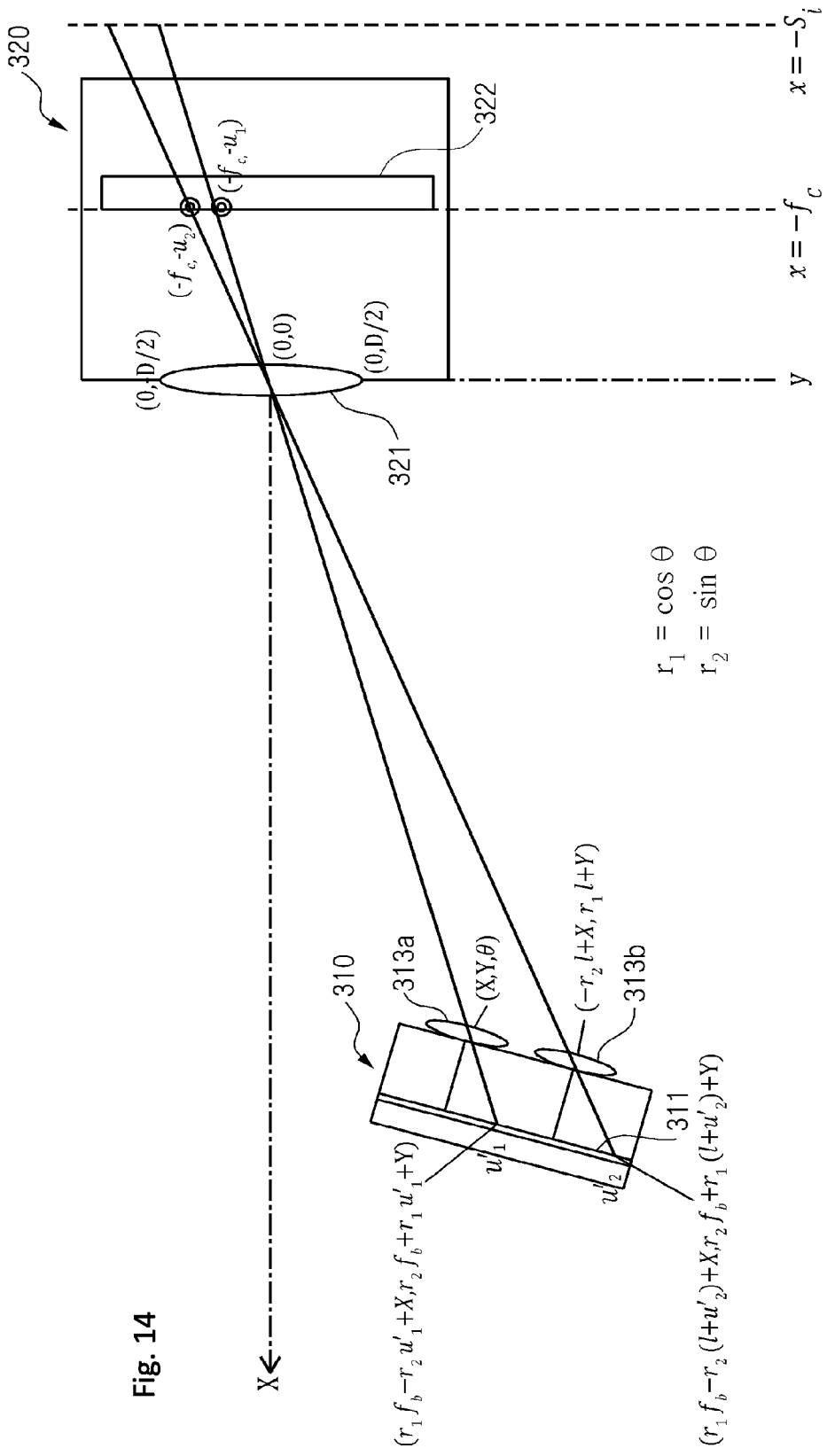
FIG. 14 is a drawing explaining a process of calculating a spatial position of a marker unit according to the third embodiment of the present invention.

FIG. 14 is a drawing explaining a process of calculating a spatial position of a marker unit according to the third embodiment of the present invention.

As shown in FIG. 14, a coordinate of an image formed on the image forming unit 320 is defined as $u_1, u_2$, a real coordinate $(X_1, Y_1)$ of the pattern portion 311, which passes a central coordinate (X,Y) of the first lens portion 313a of the marker unit 310 and meets the pattern portion 311, may be represented as a Formula 9.

$$(X_1, Y_1) = (\cos \theta f_b - \sin \theta u_1' + X, \sin \theta f_b + \cos \theta u_1' + Y) \quad \text{[Formula 9]}$$

Also, a real coordinate $(X_2, Y_2)$ of the pattern portion 311, which passes a central coordinate $(-\sin \theta 1 + X, \cos \theta 1 + Y)$ of the second lens portion 313b and meets the pattern portion 311, may be represented as Formula 10.

$$(X_2, Y_2) = (\cos \theta f_b - \sin \theta(1+u_2') + X, \sin \theta f_b + \cos \theta(1+u_2') + Y) \quad \text{[Formula 10]}$$

Meanwhile, each of coordinate of Line1 and Line2 may be represented using a Table 2 in the same manner as the second embodiment.

TABLE 2

| | Real coordinate of the pattern portion (1) | Coordinates of the first and second lens portions (2) | Coordinate of the lens portion of the image forming unit (3) | Coordinate of the enlarged pattern portion (4) |
|---|---|---|---|---|
| Line 1 | $X_1, Y_1$ | X, Y | 0, 0 | $-f_c'$, $-u1$ |
| Line 2 | $X_2, Y_2$ | $-\sin\theta_1 + X$, $\cos\theta_1 + Y$ | 0, 0 | $-f_c'$, $L + u2$ |

Table 2 is an arranged table of coordinates placed on Line1 and Line2, generating two equations using the three coordinates (2), (3) with reference to the Table 2, and (4), X,Y may be represented as Formula 11.

$$X = [(\cos \theta f_c + \sin \theta u_2)/(u_2 - u_1)]1, Y = [(\cos \theta f_c + \sin \theta u_2)/(u_2 - u_1)](lu_1/f_c) \quad \text{[Formula 11]}$$

Also, generating two equations using the three coordinates (1), (2), and (3) of the Line1 and Line2, and the difference between the two equations may be represented as Formula 12.

$$\cos \theta X(u_2' - u_1') + \sin \theta Y(u_2' - u_1') - lf = 0 \quad \text{[Formula 12]}$$

Also, generating two equations using the three coordinates (1), (2), and (4) of the Line1 and Line2, and the difference between the two equations may be represented as Formula 13.

$$\cos \theta[f_c(u_2' - u_1') - f_b(u_2 - u_1)] + \sin \theta[u_2 u_2' - u_1 u_1'] + \cos \theta X(u_2' - u_1') + \sin \theta Y(u_2' - u_1') - lf = 0 \quad \text{[Formula 13]}$$

Also, generating two equations using the three coordinates (1), (3), and (4) of the Line1 and Line2, and the two equations may be represented as Formulas 14 and 15.

$$u_1 X - f_c Y + \cos \theta(u_1 f_b - u_1' f_c) - \sin \theta(f_b f_c + u_1 u_1') = 0 \quad \text{[Formula 15]}$$

$$u_2 X - f_c Y + \cos \theta(u_2 f_b - u_2' f_c + lf_c) - \sin \theta(u_2 u_2' + lu_2 f_b) = 0 \quad \text{[Formula 16]}$$

Meanwhile, substituting the Formula 12 to the Formula 13 and dividing into $\cos \theta$, and $\tan \theta$ may be represented as Formula 16.

$$\tan \theta = \sin \theta / \cos \theta = [f_c(u_2' - u_1') - f_b(u_2 - u_1)]/(u_2 u_2' - u_1 u_1) \quad \text{[Formula 16]}$$

And, the θ value is known in the Formulas 14 and 15, the only parameter X,Y may be calculated by solving simultaneous equation constituted by the Formulas 14 and 15, and the coordinate (X,Y) of the first lens portion 313a of the marker unit 210 may be represented as Formula 17.

$$X = \{\cos \theta[f_c(u_2' - u_1') - f_b(u_2 - u_1) - lf_c] + \sin \theta(u_2 u_2' - u_1 u_1' + f_b f_c + lu_2 + f_b)\}/(u_2 - u_1)$$

$$Y = \{\cos \theta f_c(u_2' u_1' - u_1 u_2' + 1) + \sin \theta[u_1 u_2(u_1' - u_2' - 1) + u_1 f_b + u_2 f_b f_c]\}/[(u_1 - u_2) f_c] \quad \text{[Formula 17]}$$

Also, coordinate $(-\sin \theta_1 + X, \cos \theta 1 + Y)$ of the second lens portion 313b is also calculated since the coordinate of the first lens portion 313a is calculated.

Fourth Embodiment

An optical tracking system according to the present invention is substantially the same as the optical tracking system of the first embodiment except for arranging two maker units, detailed explanations of other elements except for an arrangement of an image forming unit and a marker unit is omitted.

Figure 15:
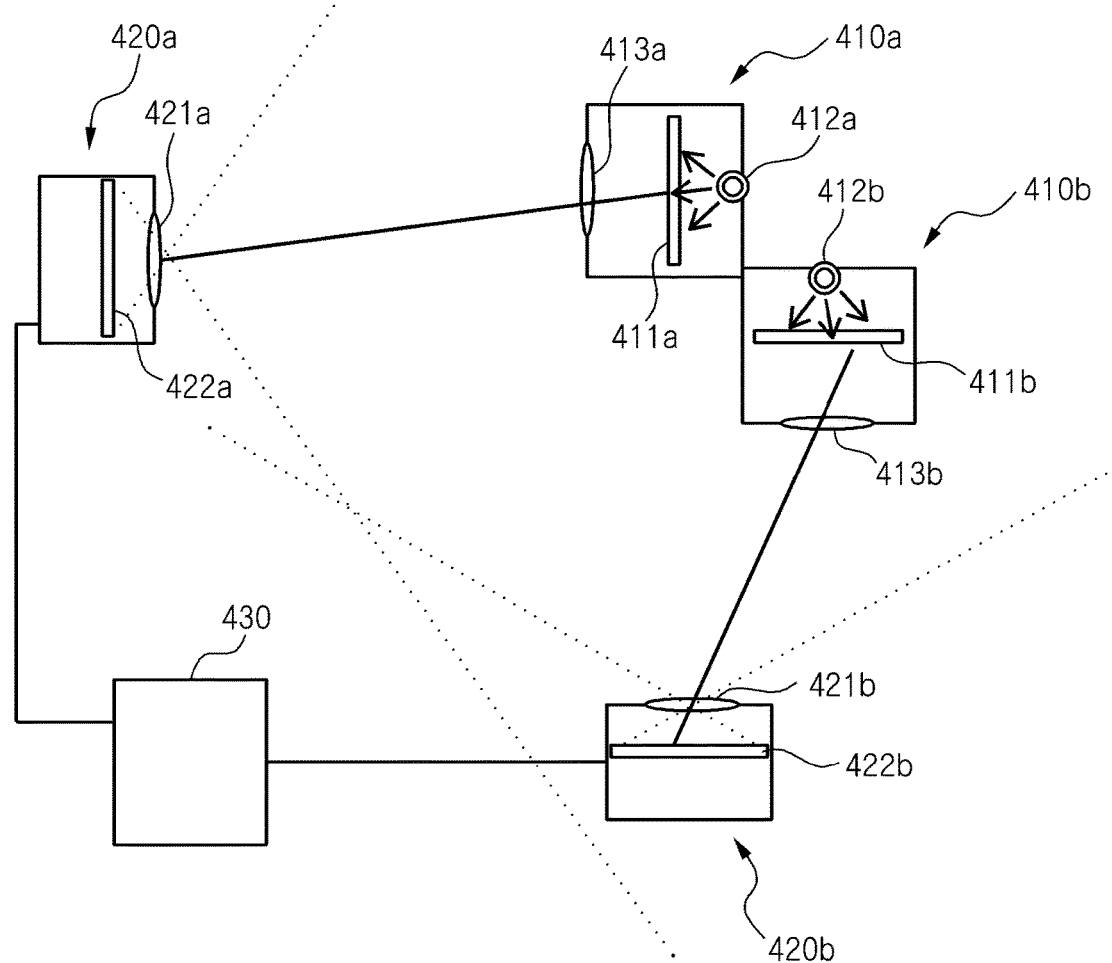
FIG. 15 is a schematic diagram of an optical tracking system according to a fourth embodiment of the present invention.

FIG. 15 is a schematic diagram of an optical tracking system according to a fourth embodiment of the present invention.

Referring to FIG. 15, an optical tracking system according to an embodiment of the present invention includes first and second marker units 410a and 410b, first and second image forming units 420a and 420b, and a processor 430.

The first and second marker units 410a and 410b are attached on a target at an interval, and a spatial position and a direction between the first and second marker units are pre-stored in the processor 430.

The first and second image forming units 420a and 420b receive parallel lights of a pattern portions 411a and 411b which are emitted from each of the first and second marker units 410a and 410b to form an enlarged image. In other words, the first image forming unit 420a forms an enlarged image by receiving the parallel light of the pattern portion 411a which is emitted from the first marker unit 420a, and the second image forming unit 420b forms an enlarged image by receiving the parallel light of the pattern portion 411b which is emitted from the second marker unit 420b.

The processor 430 is connected to the first and second image forming units 420a and 420b, and calculates a spatial position and a direction of the first and second marker units 410a and 410b by using the enlarged images of the pattern portion 411a and 411b formed on the first and second image forming units 420a and 420b.

Figure 16:
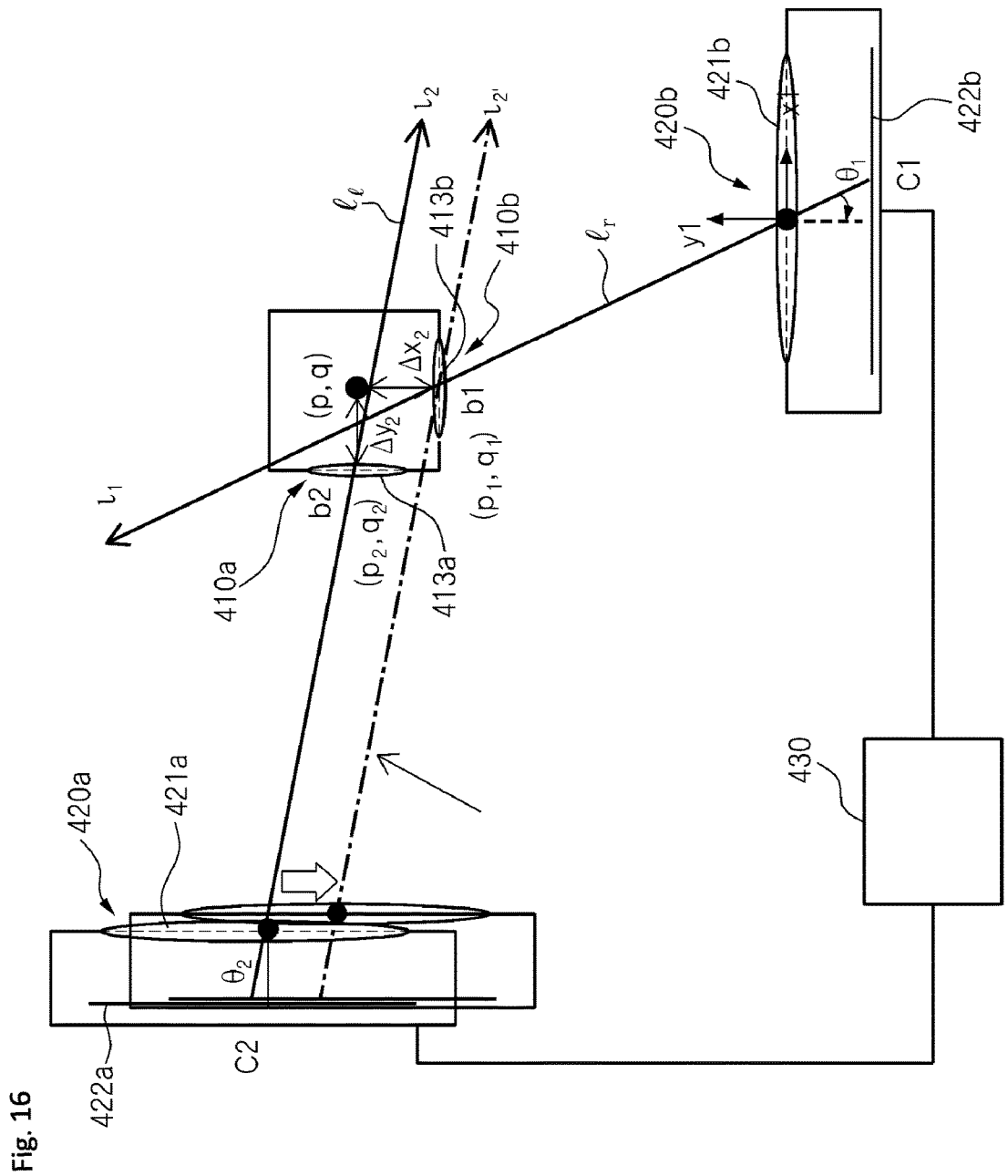
FIG. 16 is a drawing explaining a process of calculating a spatial position of a marker unit according to the fourth embodiment of the present invention.

FIG. 16 is a drawing explaining a process of calculating a spatial position of a marker unit according to the fourth embodiment of the present invention.

As shown in FIG. 16, an optical tracking system according to an embodiment of the present invention calculates through a processor 430 a vector from a center of a lens portion 421a of a first image forming unit 420a to a center of a first lens portion 413a of a first marker unit 410a, a vector from a center of a lens portion 421b of a second image forming unit 420b to a center of a second lens portion 413b of a second marker unit 410b, and a spatial position and a direction of the first and second marker units 410a and 410b by calculating an intersection point between two straight line equations of $l_1$ and $l_r$, in which the two straight line equations $l_1$ and $l_r$ are generated from the two vectors.

Fifth Embodiment

Figure 17:
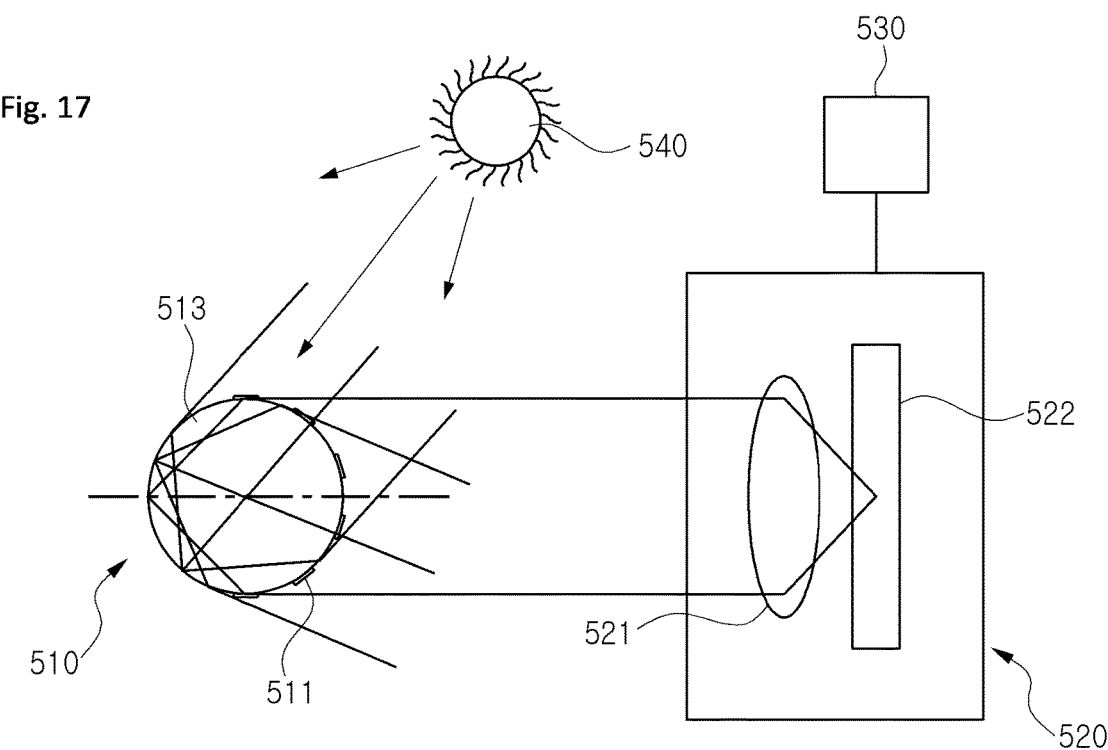
FIG. 17 is a schematic diagram of an optical tracking system according to a fifth embodiment of the present invention.

FIG. 17 is a schematic diagram of an optical tracking system according to a fifth embodiment of the present invention.

Figure 18:
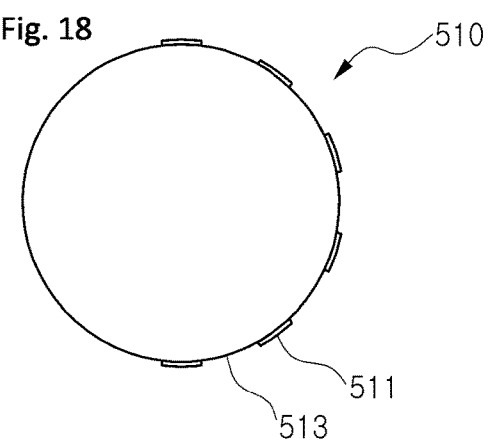
FIG. 18 is a drawing showing a marker unit according to the fifth embodiment of the present invention.

Referring to FIGS. 17 and 18, an optical tracking system according to an embodiment of the present invention includes at least one light source 540, at least one marker unit 510, at least one image forming unit 520, and a processor 530.

The at least one light source is arranged to irradiated a light toward the marker unit 410. For example, the light source 540 may be an LED (Light Emitting Diode). Herein, it may be preferable to arrange the at least one light source 540 outside the marker unit 510.

The at least one marker unit 510 reflects the light emitted from the light source 540 in a parallel light.

The marker unit 510 may include a ball lens 513 in which a pattern portion 511 is formed on a surface of the ball lens 513. Herein, the pattern portion 511 may be entirely formed on the surface of the ball lens 513. Alternatively, the pattern portion 511 may be partially formed on the surface of the ball lens 513.

The ball lens 513 reflects the light irradiated from the light source 540 toward the image forming unit 520 to form an enlarged image of the pattern portion 511 on the image forming unit 520.

The at least one image forming unit 520 receives the parallel light provided by the marker unit 510 and forms an enlarged image of the pattern portion 511.

For example, the image forming unit 520 may be a camera which receives the parallel light provided by the marker unit 510 through a lens portion 521 and forms an image of the pattern portion 511 on a sensor portion 522 which is enlarged by the parallel light.

The processor 530 calculates a spatial position of the marker unit 510 by comparing the enlarged image of the pattern portion 511 formed on the image forming unit 520 with a reference image of the pattern portion 511 stored in the processor 530.

In more detail, the processor 530 calculates a spatial position of the marker unit 510 by comparing a position and a size of an enlarged image of the pattern portion 511 formed on the image forming unit 520 with a pre stored position and size of reference image of the pattern, a direction of the marker unit 510 by comparing a position and a size of the pattern portion 511 for each area of the enlarged image of the pattern portion 511 with a pre-stored position of reference pattern portion and a size of the reference pattern portion for each area, and a spatial position and a direction of a target by using the spatial position and the direction of the marker unit 510.

A process of calculating a spatial position and a direction of a target by using the fifth embodiment is explained with reference to FIGS. 17 to 24.

Figure 19:
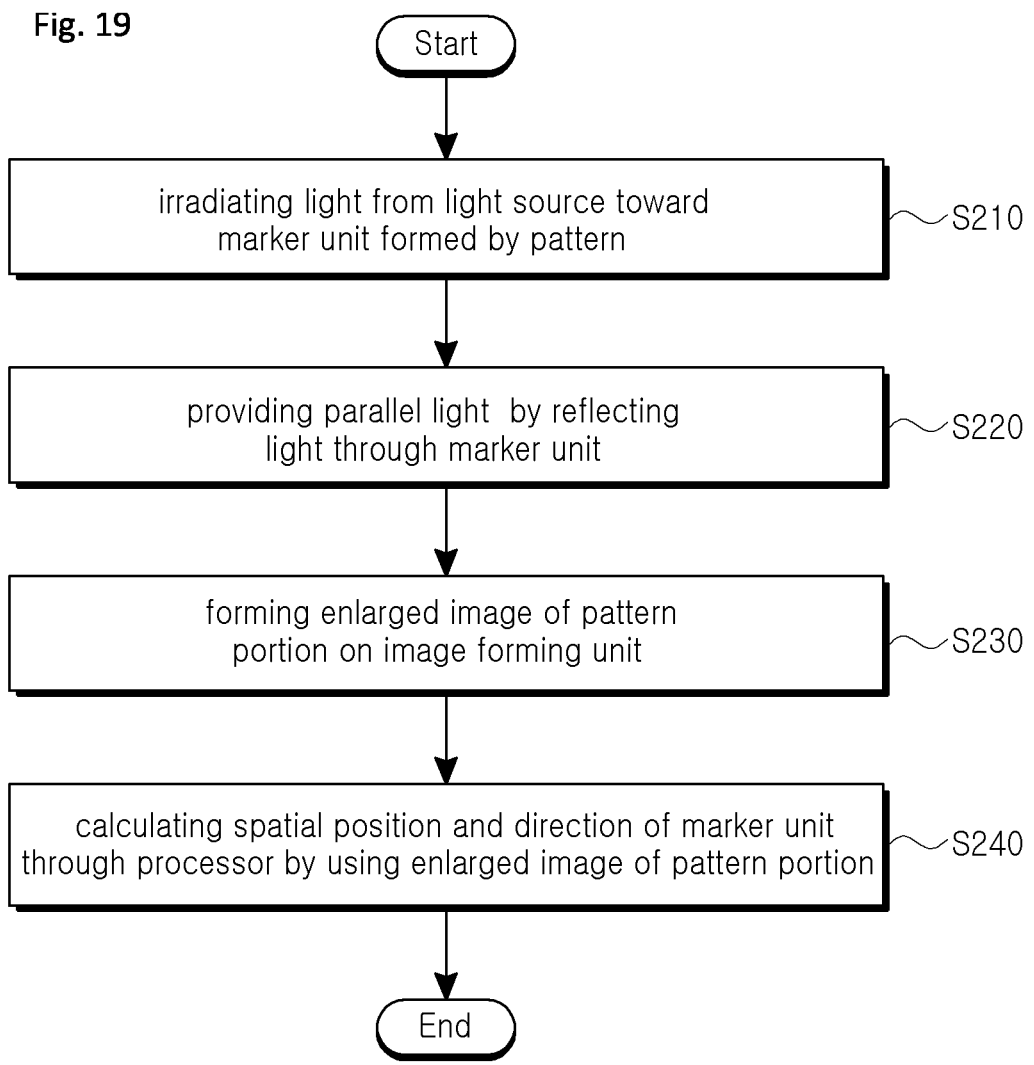
FIG. 19 is a flow chart explaining a method of tracking a target using an optical tracking system according to the fifth embodiment.

FIG. 19 is a flow chart explaining a method of tracking a target using an optical tracking system according to the fifth embodiment.

Referring to FIGS. 17-19, in order to track a target using an optical tracking system according to the fifth embodiment, first, a light is irradiated toward a marker unit 510, in other word, towards a ball lens on which a pattern portion 51 is formed, by operating a light source 540 (S210).

Then, the light irradiated toward the marker unit 510 is reflected by the pattern portion 511, which is formed on a surface of the ball lens 513, in a parallel light (S220). The parallel light reflected by the ball lens 513 is incident on an image forming unit 520 to form an enlarged image of the pattern portion 511 (S230).

Explaining the step of forming an enlarged image of the pattern portion 511 (S230) in more detail, the parallel light of the pattern portion 511 reflected by the ball lens 513 passes a lens portion 512 of the image forming unit 520, and an enlarged pattern portion 511 is formed on a sensor portion 522 by the parallel light which have passed the lens portion 521 of the image forming unit 520.

When the enlarged image of the pattern portion 511 is formed on the image forming unit 520 as described above, then, a spatial position and a direction of the marker unit 510 is calculated by using the enlarged image of the pattern portion 511 (S240).

A detailed process of calculating a spatial position and a direction of the marker unit 510 is explained below with reference to FIG. 20.

Figure 20:
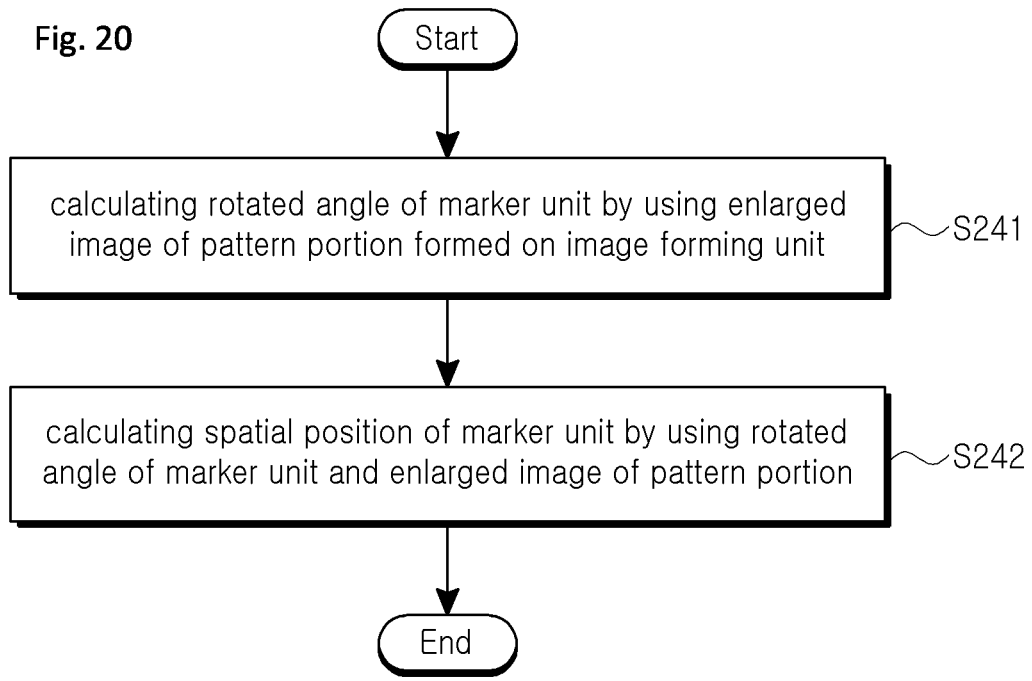
FIG. 20 is a flow chart explaining a process of calculating a spatial position and a direction of a marker unit.

FIG. 20 is a flow chart explaining a process of calculating a spatial position and a direction of a marker unit.

Referring to FIG. 20, in order to calculate a spatial position and a direction of a marker unit, a direction of the marker unit 510 is calculated through the processor 530 by calculating a rotated angle of the marker unit 510 by using the enlarged image of the pattern portion 511 formed on the image forming unit 520 (S241).

When a rotated angle of the marker unit 510 is calculated by the processor 530, a spatial position of the marker unit 510 is calculated through the processor 530 by using the enlarged image of the pattern portion 511 formed on the image forming unit 520 and the rotated angle of the marker unit 510 (S242).

Herein, a spatial position and a direction of the image forming unit 520 is pre-stored in the processor 530.

A detailed process of calculating a direction of the marker unit 510 (S241) is explained below with reference to FIGS. 21 and 22.

Figure 21:
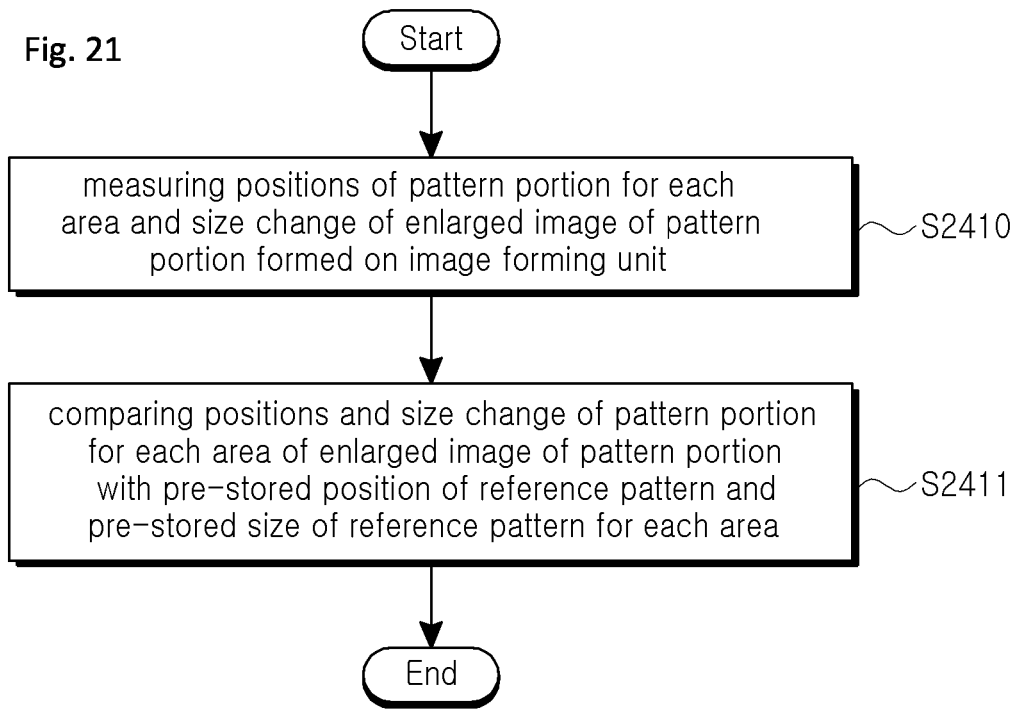
FIG. 21 is a flow chart explaining a process of calculating a direction of a marker unit.
Figure 22:
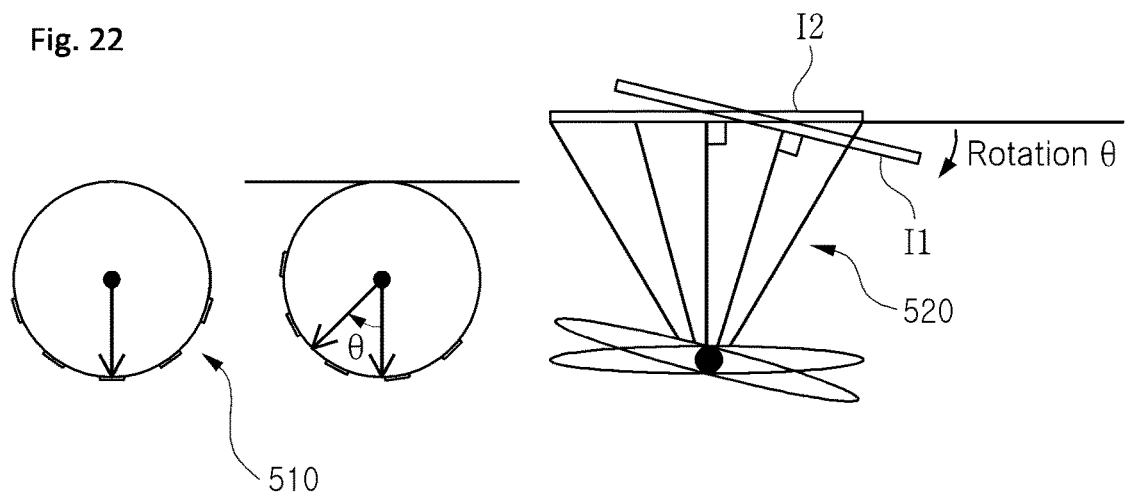
FIG. 22 is a drawing explaining a process of calculating a direction of a target using an optical tracking system of the fifth embodiment.

FIG. 21 is a flow chart explaining a process of calculating a direction of a marker unit, and FIG. 22 is a drawing explaining a process of calculating a direction of a target using an optical tracking system of the first embodiment.

Referring to FIG. 21, in order to calculate a direction of the marker unit 510, first, a position for each area of the enlarged image of the pattern portion 511 formed on the image forming unit 520 and a size change of the pattern portion 511 is measured (S1410).

After measuring the position and the size change of the pattern portion 511 for each area of the enlarged image of the pattern portion 511, then, the a direction of the marker unit 510 is calculated by calculating a rotated angle of the marker unit 510 by comparing a reference position of the pattern portion and a reference size of the pattern portion for each area which are pre-stored in the processor 530 with the position and the size change of the pattern portion 511 for each area of the enlarged image of the pattern portion 511 formed on the image forming unit 520 (S2411).

In other words, as shown in FIG. 22, the position and the size of the enlarged image of the pattern portion 511 formed on the image $I_1$ forming unit 520 is changed when the marker unit 510 is rotated, and therefore, a direction of the marker unit 510 is calculated by calculating the rotated angle θ of the marker unit 510 by comparing a position and a size change of the pattern portion 511 for each area of the enlarged image $I_1$ with the reference position of the pattern portion 511 and a reference size of pattern portion for each area of the image $I_2$ of the pattern portion 511 which are pre-stored in the processor 530.

Next, a detailed process of calculating a spatial position of the marker unit 510 (S242) is explained below with reference to FIGS. 23 to 24d.

Figure 23:
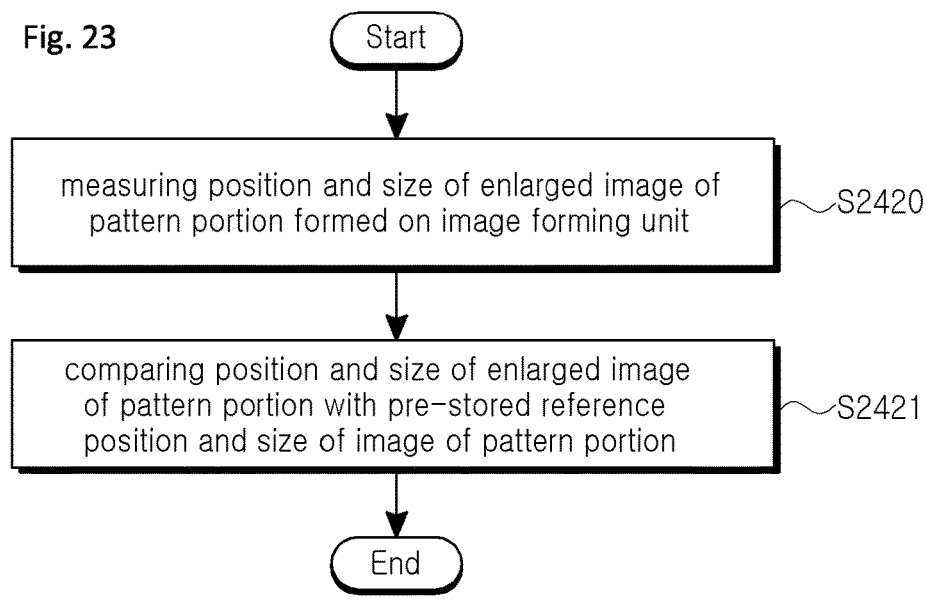
FIG. 23 is a flowchart explaining a process of calculating a spatial position of a marker unit.

FIG. 23 is a flowchart explaining a process of calculating a spatial position of a marker unit, and FIGS. 24a-24d are drawings explaining a process of calculating a spatial position of a marker unit.

Figure 24A:
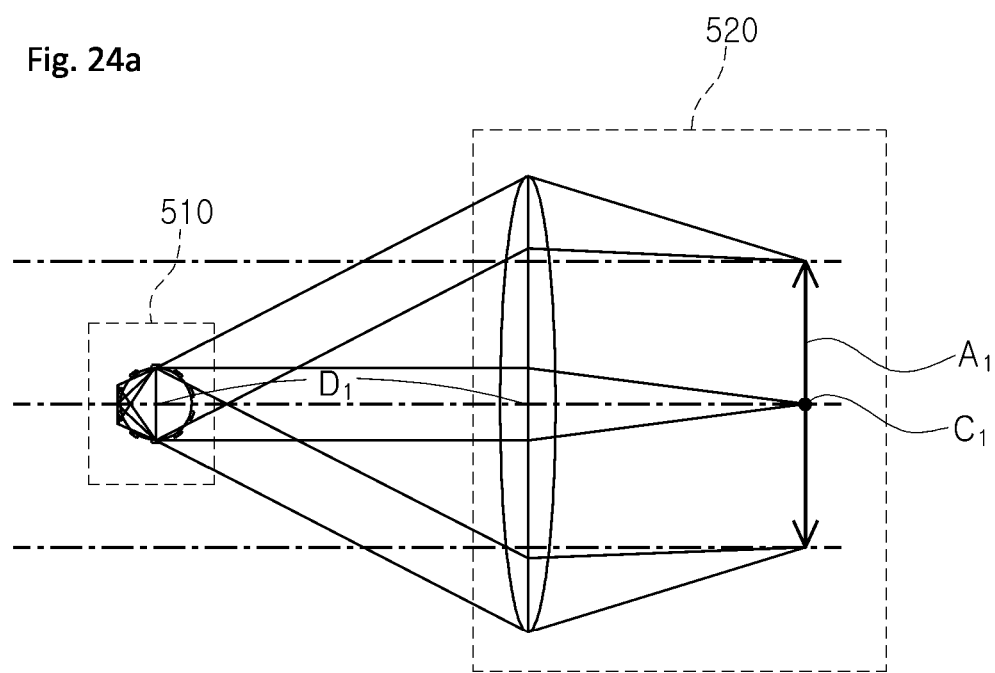
FIGS. 24a-24d are drawings explaining a process of calculating a spatial position of a marker unit.
Figure 24B:
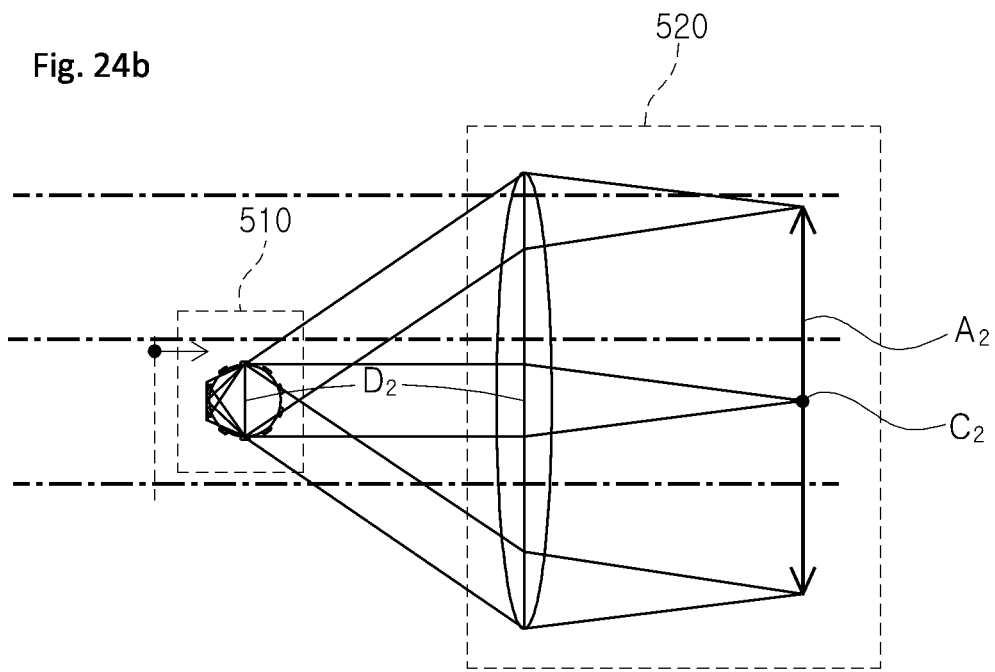
Figure 24C:
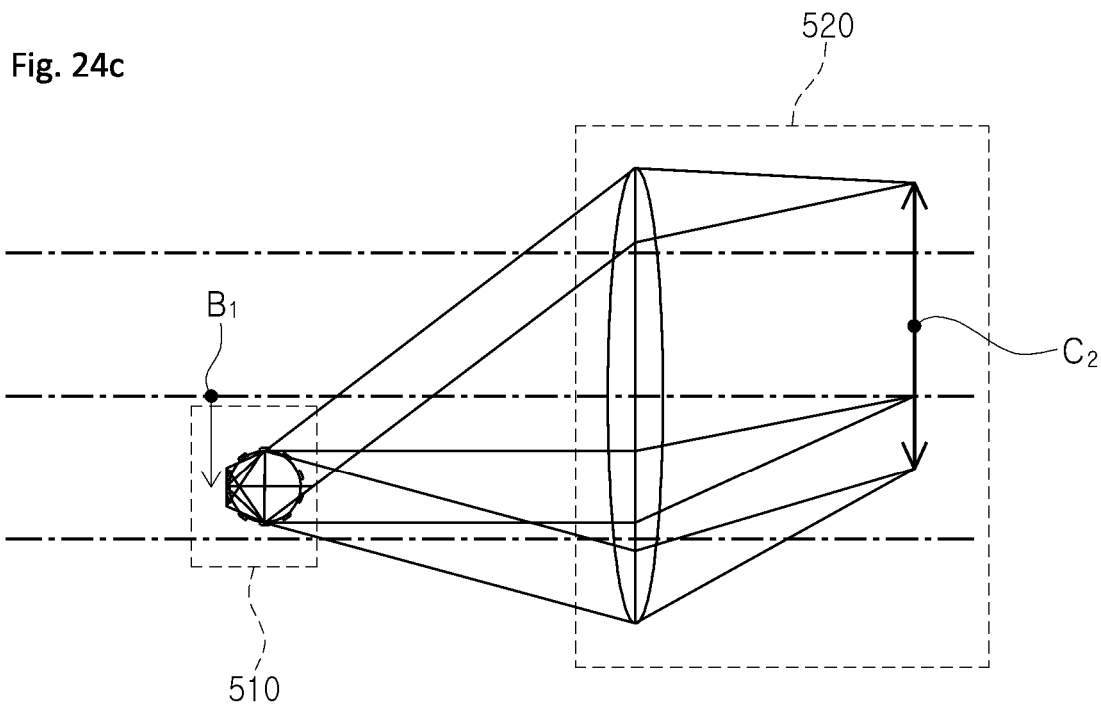
Figure 24D:
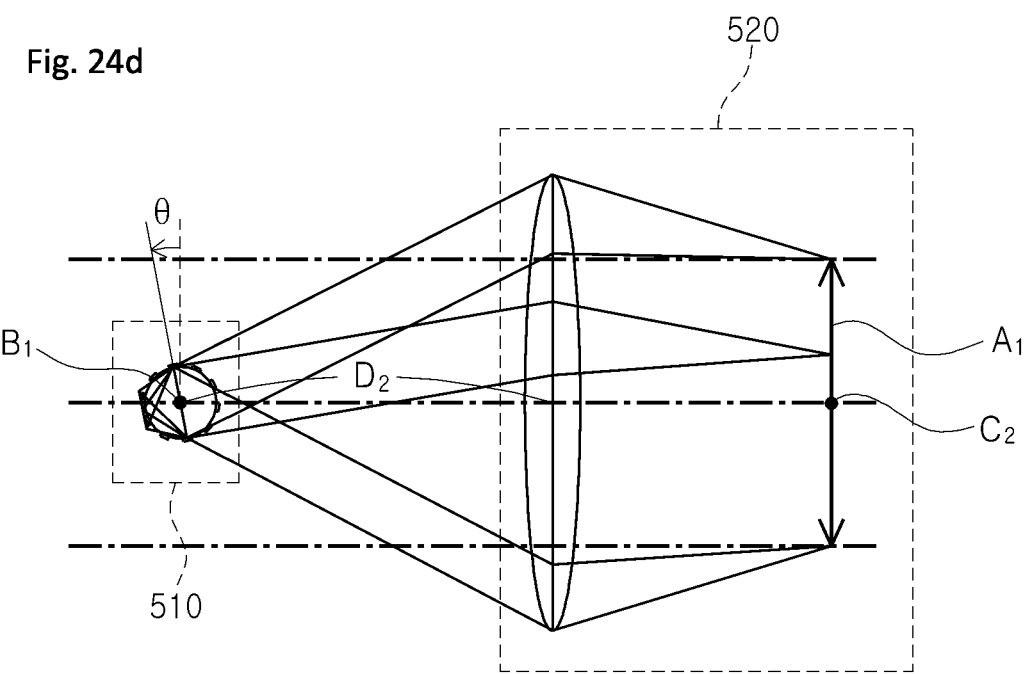

Referring to FIGS. 23 to 24d, in order to calculate a spatial position of a marker unit 510, first, a position and a size of the enlarged image of the pattern portion 511 formed on the image forming unit 520 is calculated by the processor 530 (S2420).

After calculating the position and the size of the image of the pattern portion 511, a spatial position of the marker unit 510 is calculated by comparing the position and the size of the enlarged image of the pattern portion 511 formed on the image forming unit 520 with the reference position and size of the image of the pattern portion 511 which are pre-stored in the processor 530 (S2421).

FIG. 24a shows a reference position and a size of an image of the pattern portion 511 formed on the image forming unit 520 when the marker unit 510 is at a position which is pre-stored in the processor 530, when a distance D2 between the marker unit 510 and the image forming unit 520 is shorter than a reference distance D1 as shown in FIG. 24b, a size A2 of the enlarged image of the pattern portion 511 formed on the image forming unit 520 is bigger than a reference size A1 of the image of the pattern portion 511 which is pre-stored in the processor 530. Therefore, a spatial position of the marker unit 510 is calculated through the processor 530 by comparing the enlarged image size A2 of the pattern portion 511 formed on the image forming unit 520 with the reference image size A1 of the pattern portion 511.

Meanwhile, although it is not shown in the figure, when the distance D2 between the marker unit 110 and the image forming unit 120 is longer than the reference distance D1, then, the size A2 of the enlarged image of the pattern portion 511 formed on the image forming unit 520 is smaller than the reference size A1 of the image of the pattern portion 511 which is pre-stored in the processor 530.

And, when the marker unit 510 is positioned below a reference position B1 as shown in FIG. 24c, the enlarged image of the pattern portion 511 is formed on the image forming unit 520 above a reference position C1 (Refer to FIG. 24a) which is pre-stored in the processor 530. Therefore, a spatial position of the marker unit 510 is calculated through the processor 530 by comparing the reference position C1 of the image of the pattern portion with the position C2 of the enlarged image of the pattern portion 511 formed on the image forming unit 520.

Meanwhile, although it is not shown in the figure, when the marker unit 510 is positioned above the reference position B1, then, the enlarged image of the pattern portion 511 is formed on the image forming unit 520 below the reference position C1 (Refer to FIG. 24a) which is pre-stored in the processor 530.

And, when the distance D2 between the marker unit 510 and the image forming unit 520 is different to the reference distance D1 and the marker unit 510 is not positioned at the reference position B1, a spatial position of the marker unit 510 is calculated by comparing the position C2 and the size A2 of the enlarged image formed on the image forming unit 520 with the reference position C1 and the reference size A1 of the image of the pattern portion 511 which is pre-stored in the processor 530.

Meanwhile, as shown in FIG. 24d, when the distance D2 between the marker unit 510 and the image forming unit 520 is identical to the reference distance D1, the marker unit 510 is positioned at the reference position B1 and the direction of the maker unit 510 is changed as θ, the calculated size A2 and position C2 of the enlarged image of the pattern portion 511 formed on the image forming unit 520 are identical to the reference position C1 and the reference size A1 of the image of the pattern portion 111 which is pre-stored in the processor 530. Therefore, a direction of the marker unit 511 is calculated by calculating the rotated angle of the marker unit 511 by comparing the position for each pattern portion 511a and the size change of the pattern portion 511a of the enlarged image $I_1$ of the pattern portion 511 with the reference position for each pattern portion 511a and the reference size of the pattern portion 511 of the image $I_2$ of the pattern portion 511 which are pre-stored in the processor 530.

As described above, an optical tracking system according to an embodiment of the present invention emits a parallel light of a pattern portion 511 from a marker unit 510, forms an enlarged image of the pattern portion 511 on an image forming unit 520, and calculates a spatial position of the marker unit 510 using the enlarged image of the pattern portion 511. In other words, the spatial position and the direction of a target to be calculated are calculated without a reduction of accuracy by enlarging an image of the pattern portion 511 and forming the image on the image forming unit 520, and therefore, an accuracy of the position of the marker unit is not dependent to a resolving power.

Therefore, an optical tracking system and a method using the same according to an embodiment of the present invention has an effect of expanding an available area by detecting an exact spatial position and a direction of a target regardless of a distance from the target to be calculated, as well as, a system downsizing is also achieved compared with conventional system by reducing size of a marker unit 510.

Sixth Embodiment

An optical tracking system according to a sixth embodiment of the present invention is described below with reference to FIG. 25.

Figure 25:
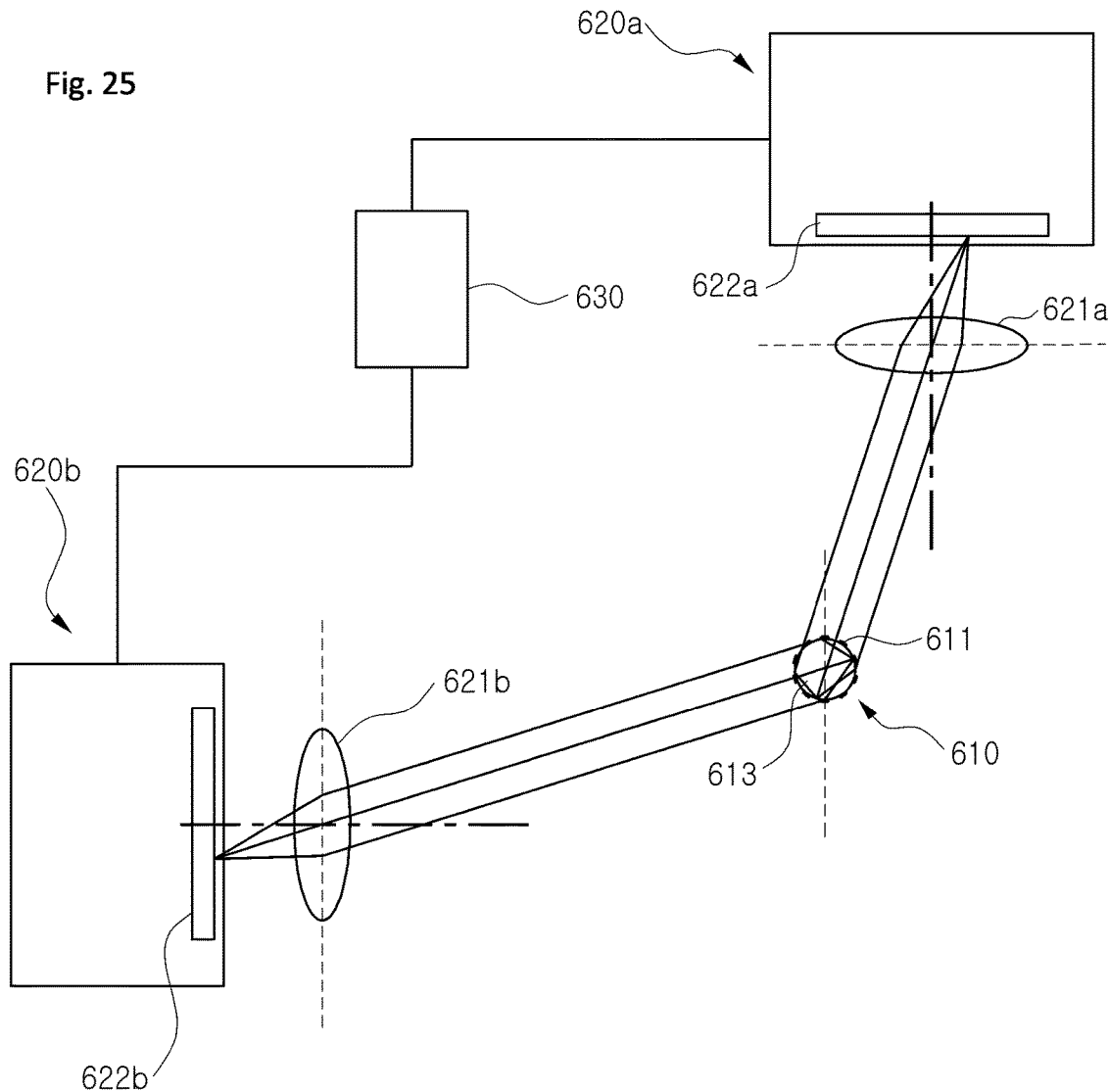
FIG. 25 is a schematic diagram of an optical tracking system according to a sixth embodiment of the present invention.

FIG. 25 is a schematic diagram of an optical tracking system according to a sixth embodiment of the present invention.

Referring to FIG. 25, an optical tracking system according to an embodiment of the present invention may include at least one light source (not shown), a maker unit 610, first and second image forming units 620A and 620B, and a processor 630.

As shown in FIG. 25, an optical tracking system according to an embodiment may be formed by a maker unit 610 in which a pattern portion 611 is formed on a surface of the marker unit 610, first and second image forming units 620a and 620b arranged with the marker unit 610 as the center, and the processor connected to the first and second image forming units 620a and 620b.

Therefore, each of the first and second image forming units 620a and 620b receives a parallel light provided by the marker unit 610 and forms an enlarged image of the pattern portion 611, for example, the image forming units 620a and 620b may be a camera which receives the parallel light provided by the marker unit 610 through each of lens portions 621a and 621b and forms images of the pattern portion 611 which are enlarged by the parallel light on each sensor portions 622a and 622b.

The processor 630 calculates a spatial position and a direction of the marker unit 610 by comparing the enlarged image of the pattern portion 611 formed on each of the first and second image forming units 620a and 620b with a reference image of the pattern portion which is pre-stored in the processor 630. Herein, a spatial position and a direction of the first and second image forming units 620a and 620b and the at least one light source are pre-stored in the processor 630.

Seventh Embodiment

An optical tracking system according to a seventh embodiment of the present invention is described below with reference to FIG. 26.

Figure 26:
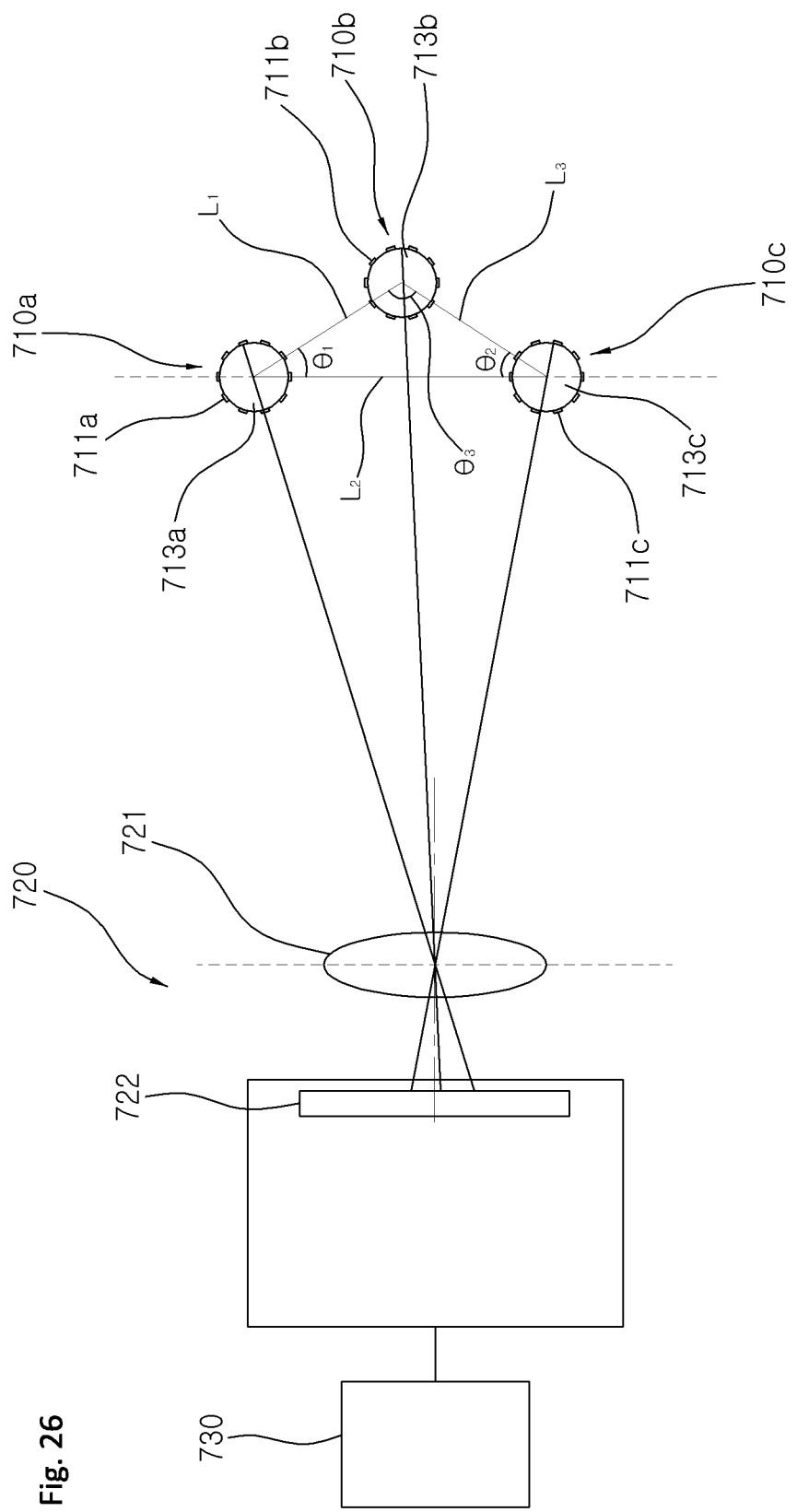
FIG. 26 is a schematic diagram of an optical tracking system according to a seventh embodiment of the present invention.

FIG. 26 is a schematic diagram of an optical tracking system according to a seventh embodiment of the present invention.

Referring to FIG. 26, an optical tracking system according to an embodiment of the present invention may include at least one light source (not shown), first to third marker units 710a 710b and 710c, an image forming unit 720, and a processor 730.

As shown in FIG. 26, in an optical tracking system according to an embodiment, first to third maker units 711a 710b and 710c, in which ball lenses 713a 713b and 713c are formed with pattern portions 711a 711b 711c on their surfaces in the first to third maker units 711a 710b and 710c, are arranged on a target at an interval, the first to third marker units 710a 710b and 710c reflect a light emitted from the light source in a parallel light, and the image forming unit 720 receives the parallel light emitted from the first to third marker units 710a 710b and 710c and forms an enlarged image of pattern portions 711a 711b and 711c.

Meanwhile, the processor 730 calculates a spatial position and a direction of the marker unit 710 by comparing the enlarged image of the pattern portion 711a 711b and 711c of the first to third marker units 710a 710b and 710c formed on the image forming unit 720 with a reference image of the pattern portion which is pre-stored in the processor 730. Herein, a spatial position and a direction of the image forming unit 720 and the at least one light source are pre-stored in the processor 730.

Also, geometric information of the first to third marker units 710a 710b and 710c attached on the target are pre-stored in the processor 730.

Herein, the geometric information of the first to third marker units 710a 710b and 710c may be length information of straight lines L1 L2 and L3 which virtually connect the adjacent marker units 710a 710b and 710c and angle information θ1 θ2 and θ3 formed by the pair of straight lines L1 L2 L3 which virtually connect the adjacent marker units 710a 710b and 710c.

Eighth Embodiment

An optical tracking system according to an eighth embodiment of the present invention is described below with reference to FIG. 27.

Figure 27:
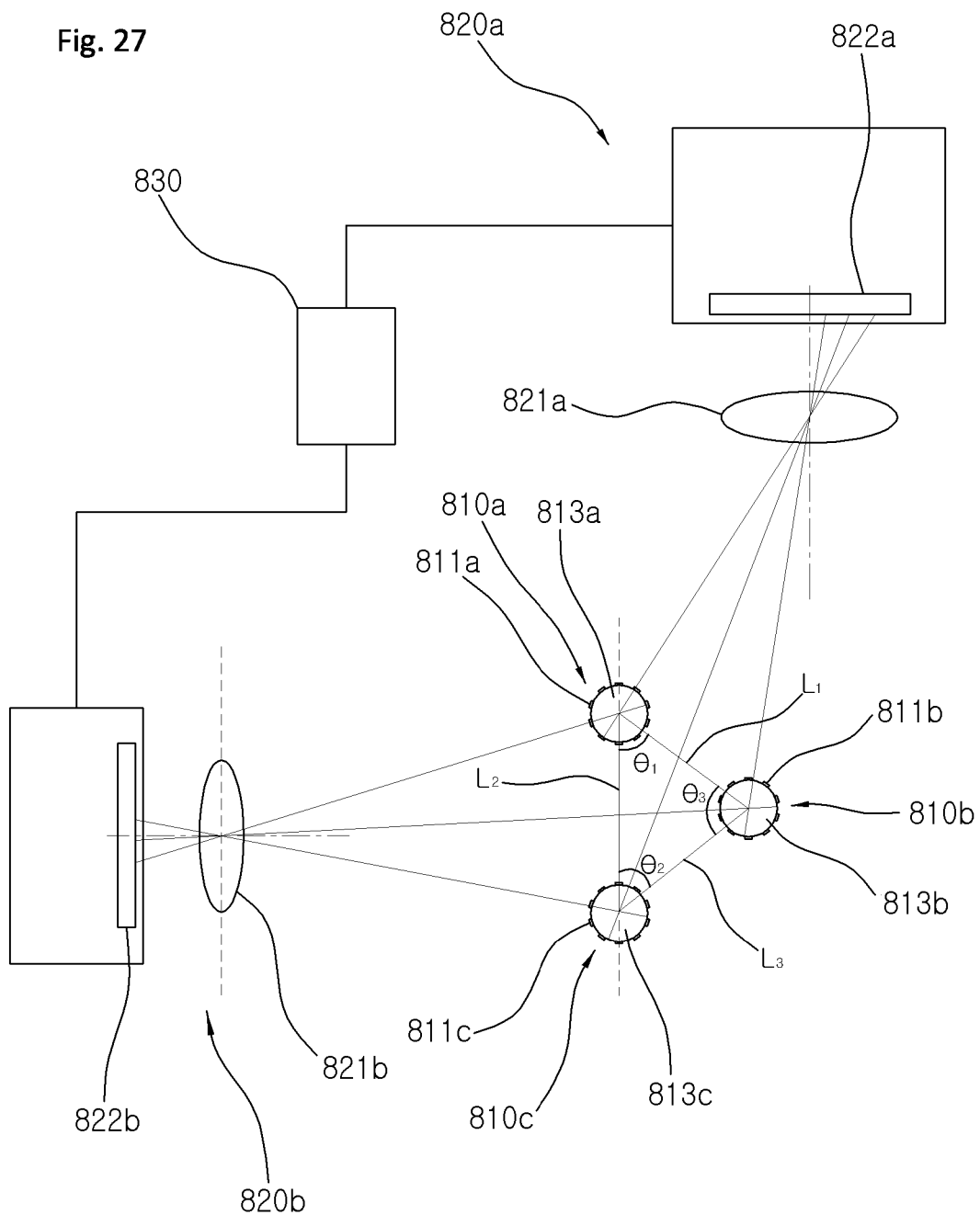
FIG. 27 is a schematic diagram of an optical tracking system according to an eighth embodiment of the present invention.

FIG. 27 is a schematic diagram of an optical tracking system according to an eighth embodiment of the present invention.

Referring to FIG. 27, an optical tracking system according to an embodiment is substantially the same as the seventh embodiment except for an addition of a second image forming unit 820b.

In other words, as shown in FIG. 27, in an optical tracking system according to an embodiment, the first to third marker units 810a 810b and 810c, in which pattern portions 811a 811b and 811c are formed on surfaces of ball lenses 813a 83b and 813c included in the first to third marker units 810a 810b and 810c, are attached on a target at an interval, and first and second image forming units 820a and 820b are arranged with the first to third marker units 810a 810b and 810c as the center, and a processor 830 is connected to the first and second image forming units 820a and 820b.

And, the image forming units 820a and 820b receive a light emitted from the light source which is reflected by the first to third marker units 810a 810b in a parallel light and form enlarged images of the pattern portions 811a 811b and 811c.

The image forming units 820a and 820b receive the parallel light emitted from the first to third marker units 810a 80b and 810c through a lens portions 821a and 821b and form enlarged images of the pattern portions 811a 811b and 811c on a sensor portions 822a and 822b.

Ninth Embodiment

An optical tracking system according to an embodiment is substantially the same as the fifth embodiment except for some details of a marker unit, detailed explanations of other elements except for some content associated with a marker unit are omitted.

Figure 28:
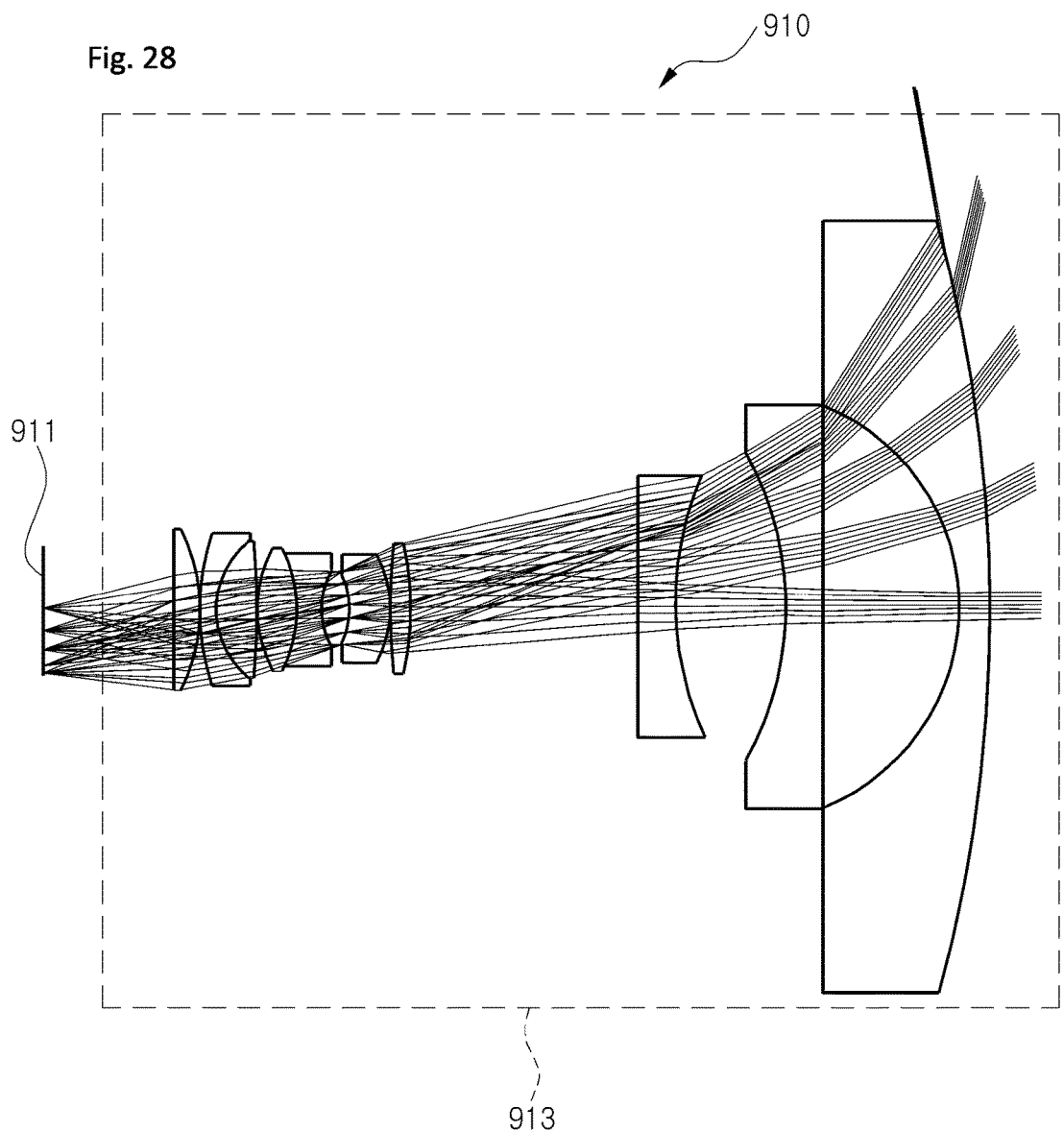
FIG. 28 is a schematic diagram of an optical tracking system according to a ninth embodiment of the present invention.

FIG. 28 is a schematic diagram of an optical tracking system according to a ninth embodiment of the present invention.

Referring to FIG. 28, a marker unit 910 of an optical tracking system according to an embodiment of the present invention may include a pattern portion 911 and a fisheye lens 913.

The pattern portion 911 may reflect or pass a light emitted from at least one light source (not shown). In other words, it may be preferable to make the pattern portion 91 to reflect the light emitted from the light source when the light source is arranged outside the marker unit 910, or to pass the light emitted from the light source when the light source is arranged inside the marker unit 910.

The fisheye lens 913 is arranged in front of the pattern portion 911 to pass and release the light, which is emitted from the light source and reflected by or having passed the pattern portion 911, toward an image forming unit (not shown) in parallel light shape.

Herein, it may be preferable to arrange the pattern portion 911 at a focal length of the fisheye lens 913.

Tenth Embodiment

An optical tracking system according to an embodiment is substantially the same as the first embodiment except for some details of a maker unit, detailed explanations of other elements except for some content associated with a marker unit are omitted.

Figure 29:
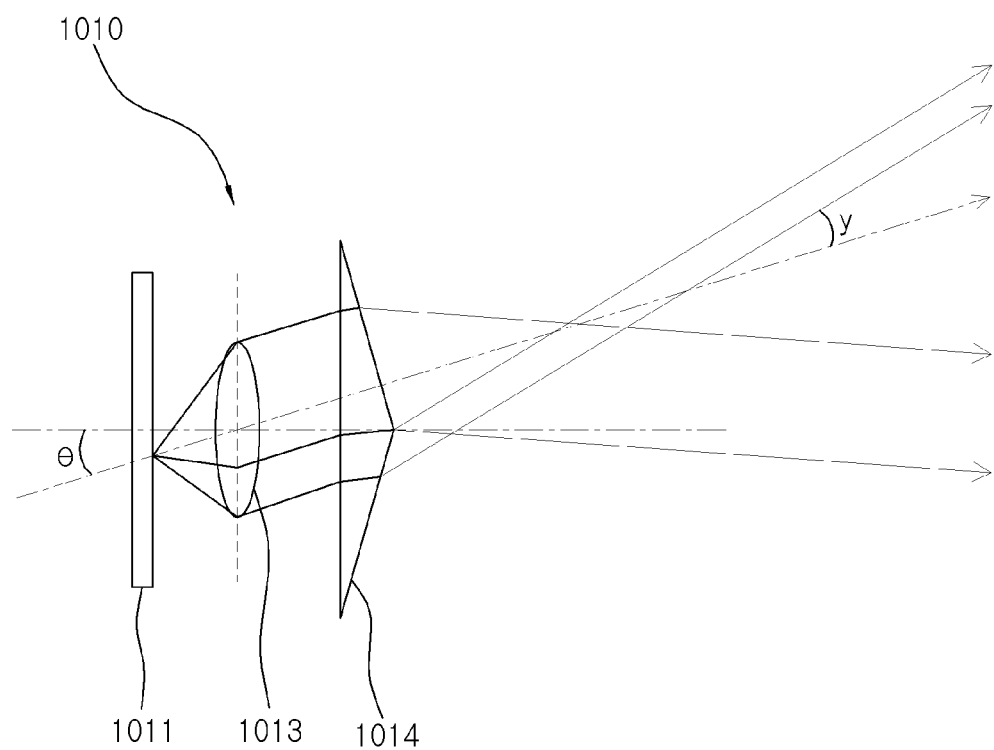
FIG. 29 is a schematic diagram of an optical tracking system according to a tenth embodiment of the present invention.

FIG. 29 is a schematic diagram of an optical tracking system according to a tenth embodiment of the present invention.

Referring to FIG. 29, a marker unit 1010 of an optical tracking according to an embodiment of the present invention may include a pattern portion 1011, an objective lens 1013, and a prism 1014.

The pattern portion 1011 may reflect or pass a light emitted from at least one light source (not shown). In other words, it may be preferable to make the pattern portion 1011 to reflect the light emitted from the light source when the light source is arranged outside the marker unit 1010, or to pass the light emitted from the light source when the light source is arranged inside the marker unit 1010.

The objective lens 1013 is arranged in front of the pattern portion 1011 to pass and release the light, which is emitted from the light source and reflected by or having passed the pattern portion 1011, toward an image forming unit (not shown) in parallel light form.

Herein, it may be preferable to arrange the pattern portion 1011 at a focal length of the objective lens 1013.

The prism 1014 passes the light having passed the objective lens 1013 and makes the light to be incident on an image forming unit after extending an angle of view of the parallel light. Herein, it may be preferable to form the prism 1014 in a pyramid shape.

Eleventh Embodiment

Figure 30:
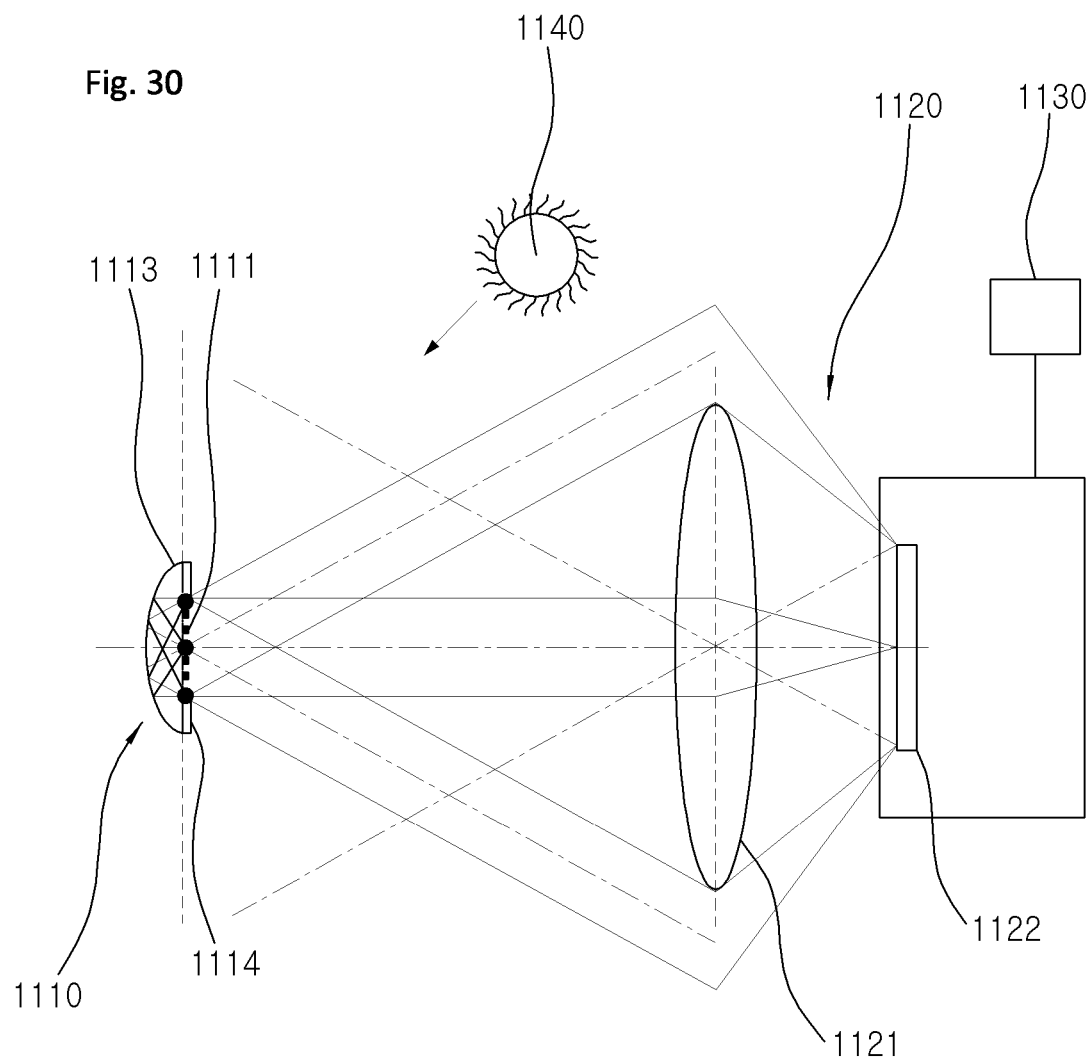
FIG. 30 is a schematic diagram of an optical tracking system according to an eleventh embodiment of the present invention.
Figure 31:
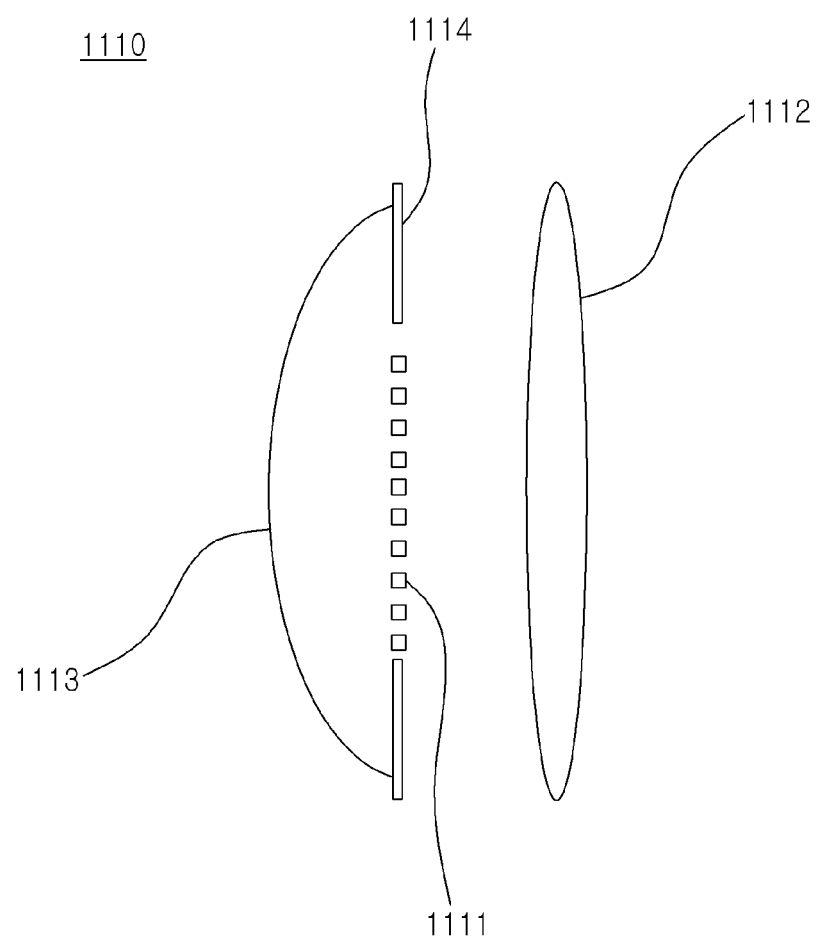
FIG. 31 is a drawing showing a marker unit according to the eleventh embodiment of the present invention.

FIG. 30 is a schematic diagram of an optical tracking system according to an eleventh embodiment of the present invention, and FIG. 31 is a drawing showing a marker unit according to the eleventh embodiment of the present invention.

Figure 32:
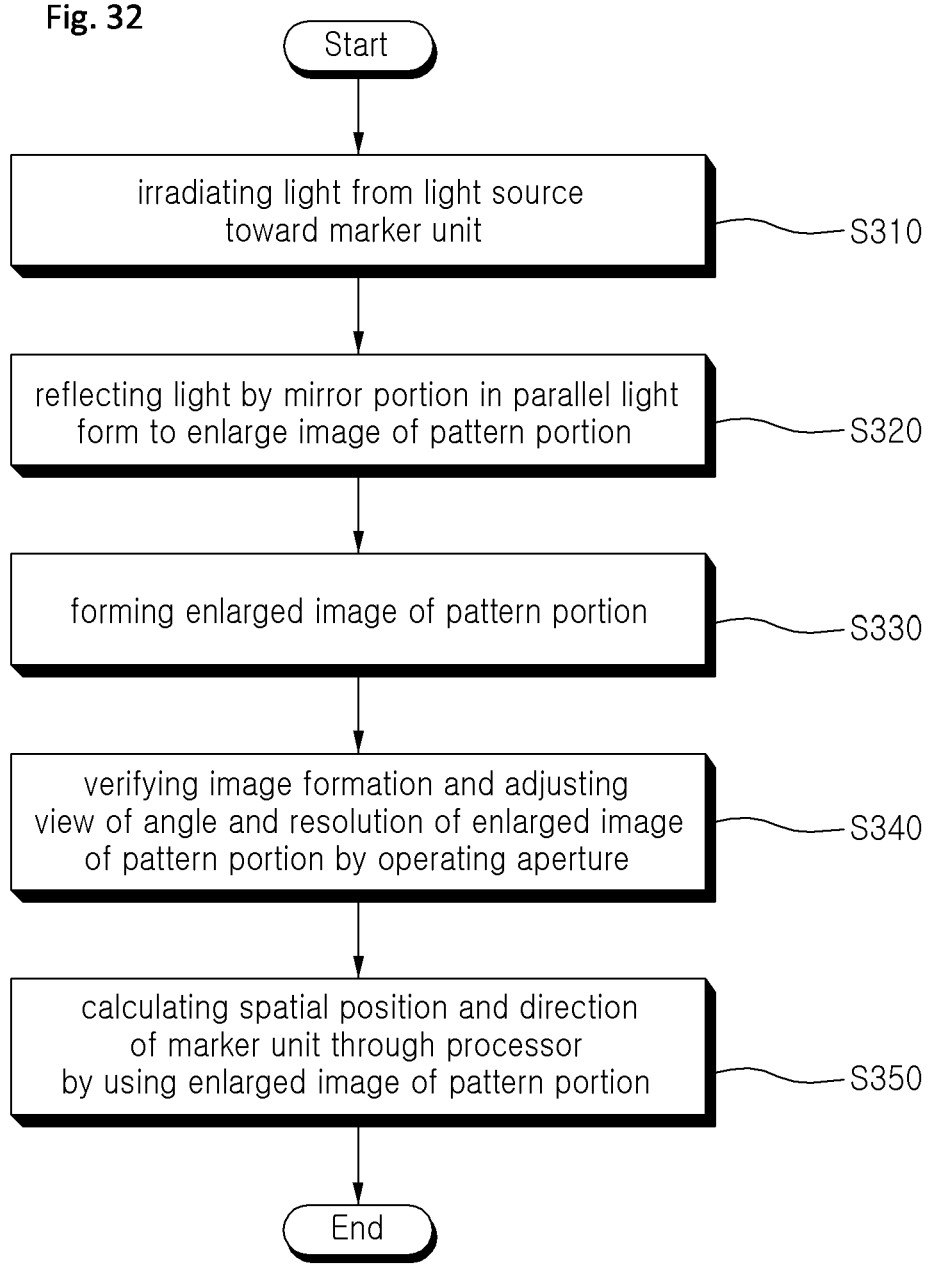
FIG. 32 is a flow chart explaining a process of calculating a direction of a target according to the eleventh embodiment of the present invention.

Referring to FIGS. 31 and 32, an optical tracking system according to an embodiment of the present invention includes at least one light source 1140, at least one marker unit 1110, at least one image forming unit 1120, and a processor 1130.

The at least one light source 140 is arranged to emit a light toward the marker unit 1110. For example, the light source may be an LED (Light Emitting Diode). Herein, it may be preferable to arrange the at least one light source 1140 outside the marker unit 1110.

The at least one marker unit 1110 reflects the light emitted from the light source 1140 in a parallel light, and an enlarged image of the pattern portion 1111 is formed on the image forming unit 1120 by the parallel light.

The marker unit 1110 may include a mirror portion 1113 and a pattern portion 1111.

The mirror portion 1113 reflects the light, which is emitted from the at least one light source 1140 toward the marker unit 1110, toward the pattern portion 1111, re-reflects the light reflected by the pattern portion 1111, and provides the light toward the image forming unit in a parallel light form. Herein, the mirror portion 1113 is a mirror with a spherical or non-spherical shape. For example, a concave mirror may be used as the mirror portion 1113 to gather and reflect the light in one point.

The pattern portion 1111 is arranged at a focal distance of the mirror portion 1113 to re-reflect the incident light which is reflected by the mirror portion 1113.

Meanwhile, the marker unit 1110 may further include a first lens 1112.

The first lens 1112 may be arranged at a focal length of the mirror portion 1113. In other words, the first lens 1112 is arranged at a location apart from the mirror portion 1113 by a focal distance of the mirror portion 1113 such that the parallel light reflected by the mirror portion 1113 is provided once more in parallel light form toward the at least one image forming unit 1120.

Meanwhile, the marker unit 1110 may further include an aperture installed on the mirror portion 1113. The aperture 1114 adjusts a light quantity of the light, which is emitted from the light source 1140 and incident on the mirror portion 1113, to adjust an angle of view and a resolution of an enlarged image of the pattern portion 1111.

The at least one image forming unit 1120 forms an enlarged image of the pattern portion 1111 by receiving the parallel light which is provided from the marker unit 1110.

For example, the image forming unit 1120 may be a camera which receives the parallel light provided by the marker unit 1110 through the pattern portion 1111 and forms an enlarged image of the pattern portion 1111 on an image sensor portion 1122.

The processor 1130 calculates a spatial position and a direction of the marker unit 1110 by comparing the enlarged image of the pattern portion 1111 with a reference image of the pattern portion pre-stored in the processor 1130.

In more detail, the processor 1130 calculates a spatial position and a direction of the marker unit 1110 by comparing a position and a size of the enlarged image of the pattern portion 1111 formed on the image forming unit 1120 with a pre-stored reference position and size of a reference image of the pattern portion 1111, a direction of the marker unit 1110 by comparing a position and a size of the pattern portion 1111 for each area of the enlarged image of the pattern portion 1111 with a pre-stored reference position and reference size of the image of the pattern portion 1111 for each area, and therefore, calculates a spatial position and a direction of a target by using the spatial position and direction of the marker unit 1110.

A process of calculating a spatial position and a direction of a target according to the eleventh embodiment is described below with reference to FIGS. 30-37.

FIG. 32 is a flow chart explaining a process of calculating a direction of a target according to the eleventh embodiment of the present invention.

Referring to FIGS. 32-32, in order to track a target using an optical tracking system according to the eleventh embodiment, first, a light is irradiated toward a maker unit 1110 by operating a light source 1140, in other words, the light is irradiated toward a mirror portion 1113 on which a pattern portion is formed on (S310).

The light irradiated toward the marker unit 1110 is reflected by marker unit 1110, in which the pattern portion 1111 is formed at a focal length of the mirror portion 1113, in a parallel light to form an enlarged image of the pattern portion 1111 (S320).

In more detail, the light irradiated toward the marker unit 1110 is reflected by the mirror portion and gathered in one point of the pattern portion 1111, re-reflected by the pattern portion 1111 and the mirror portion 1113 in a parallel light, and the parallel light is emitted once more in a parallel light through a first lens 1112.

The parallel light reflected by the marker unit 1110 is incident on an image forming unit and forms an enlarged image of the pattern portion 1111 (S330).

Explaining in detail the process of forming the enlarged image of the pattern portion 1111, the parallel light of the pattern portion 1111 which is reflected by the marker unit 1110 passes a lens portion 1121 of the image forming unit 1120, the parallel light, which have passed the lens portion 1121 of the image forming unit 1120, forms the enlarged image of the pattern portion 1111 on a sensor part 1122.

When the enlarged image of the pattern portion 1111 is formed on the image forming unit 1120, an angle of view and a resolution of the enlarged image of the pattern portion 1111 are adjusted by adjusting a light quantity of the light which is incident on the mirror portion 1113 by operating an aperture 1114 after verifying an image formation (S340).

After adjusting the view of angle and the resolution of the enlarged image of the pattern portion 1111 by adjusting the light quantity of the light which is incident on the mirror portion by the aperture 1114, a spatial position and a direction of the marker unit 1110 are calculated through the processor 1130 by using the enlarged image of the pattern portion 1111 in which the view of angle and the resolution are adjusted (S350).

The process of calculating the spatial position and the direction of the marker unit 1110 (S150) is described below with reference to FIG. 33.

Figure 33:
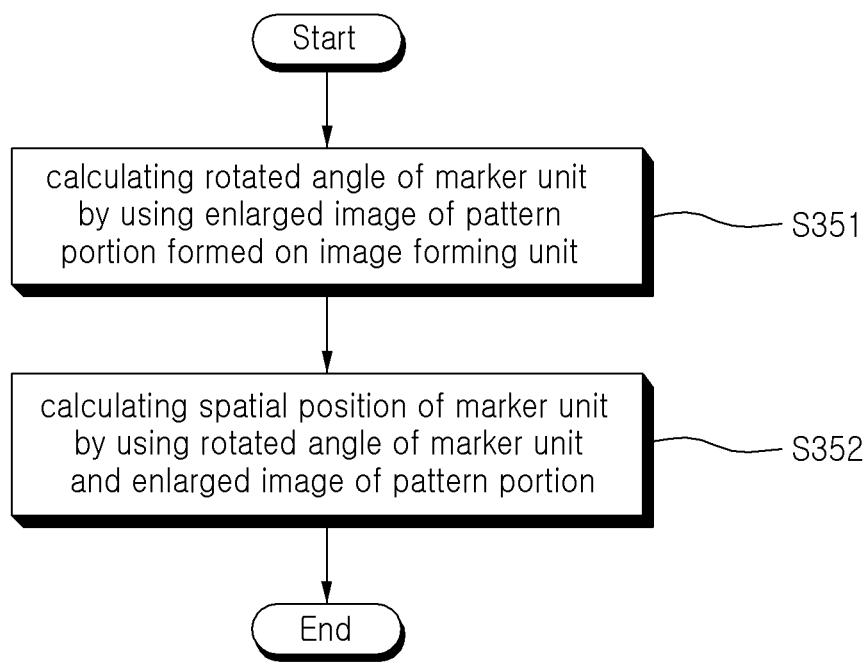
FIG. 33 is a flow chart explaining a spatial position and a direction of a marker unit.

FIG. 33 is a flow chart explaining a spatial position and a direction of a marker unit.

Referring to FIG. 33, in order to calculate a spatial position and a direction of the marker unit 1110 through the processor 1130, the direction of the marker unit 1110 is calculated by calculating a rotated angle of the marker unit 1110 by using the enlarged image of the pattern portion 1111 formed on the image forming unit 1120 (S351).

After calculating the rotated angle of the marker unit 1110 through the processor 1130, the spatial position of the marker unit 1110 is calculated through the processor 1130 by using the enlarged image of the pattern portion 1111 formed on the image forming unit 1120 and the rotated angle of the marker unit 1110 (S352).

Herein, a spatial position and a direction of the image forming unit 1120 are pre-stored in the processor 1130.

A detailed process of calculating the direction of the marker unit 1110 (S351) is described below with reference to FIGS. 34 and 35.

Figure 34:
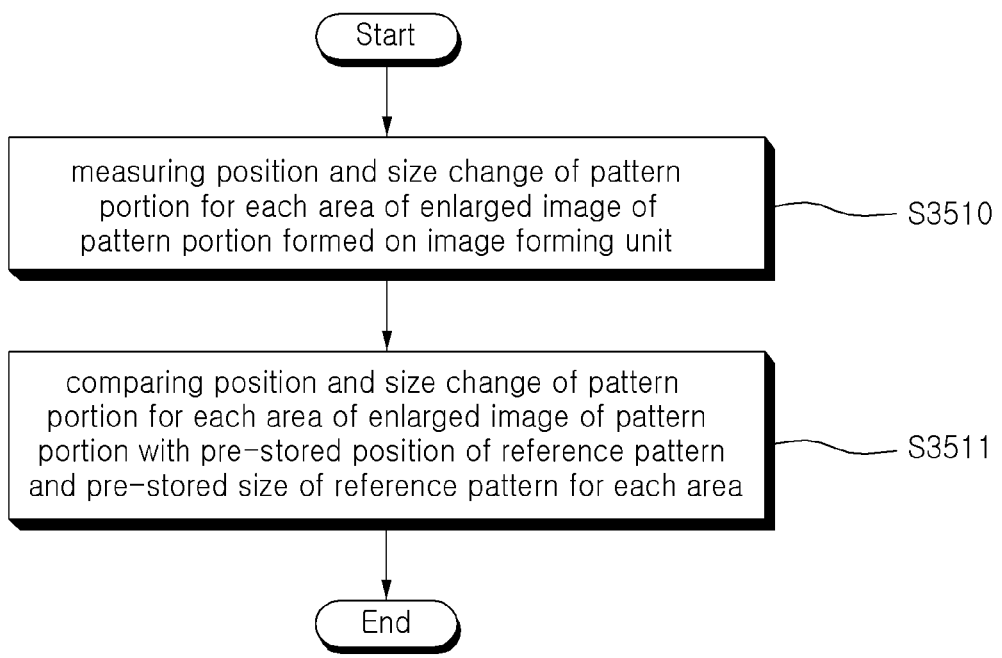
FIG. 34 is a flow chart explaining a direction of a marker unit.
Figure 35:
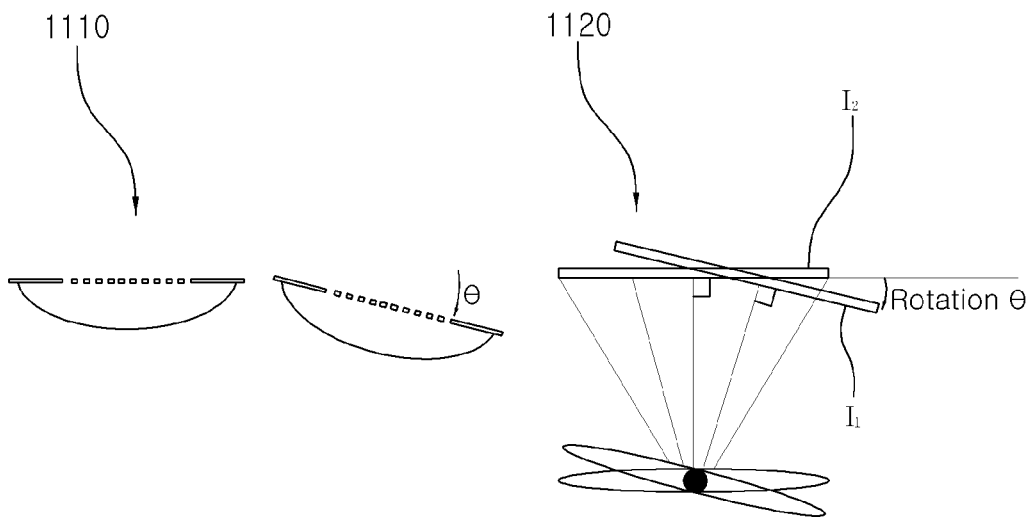
FIG. 35 is a drawing explaining a process of calculating a direction of a target using an optical tracking system of the eleventh embodiment.

FIG. 34 is a flow chart explaining a direction of a marker unit, and FIG. 35 is a drawing explaining a process of calculating a direction of a target using an optical tracking system of the eleventh embodiment.

Referring to FIG. 34, in order to calculated the direction of the marker unit 1110, first, positions for each area of pattern portion 1111 and a size change of the pattern portion 1111 of the enlarged image of the pattern portion 1111 are measured (S3510).

After measuring the positions for each area of pattern portion 1111 and the size change of the pattern portion 1111, the direction of the marker unit 1110 is calculated by calculating the rotated angle of the marker unit 1110 by comparing the position and the size change of the pattern portion 1111 for each area of the enlarged image of the pattern portion 1111 formed on the image forming unit 1120 with a reference position of and a reference size of the pattern portion for each area of an image of the pattern portion 1111 which are pre-stored in the processor 1130 (S3511).

In other words, as shown in FIG. 35, a position and a size of the pattern portion 1111 of the enlarged image $I_1$ of the pattern portion 1111 formed on the image forming unit 1120 are changed as the marker unit 1110 is rotated, and the processor 1130 calculates the direction of the marker unit 1110 by calculating the rotated angle of the marker unit 1110 by comparing the position and the size change of the pattern portion 1111 for each area of the enlarged image $I_1$ of the pattern portion 1111 formed on the image forming unit 1120 with the reference position and the reference size change for each area of the pattern portion 1111 of the enlarged pattern image of the pattern portion, which are pre-stored in the processor 1130.

Next, a detailed process of calculating the spatial position of the marker unit 1110 (S352) is described below with reference to FIGS. 36 and 37.

Figure 36:
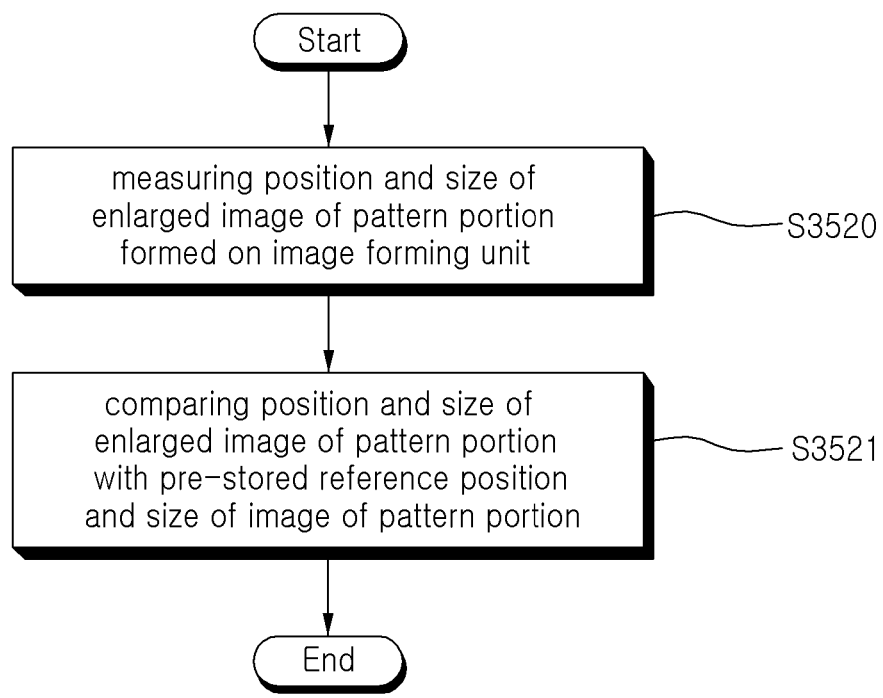
FIG. 36 is a flow chart explaining a spatial position of a marker unit.

FIG. 36 is a flow chart explaining a spatial position of a marker unit, and FIGS. 37a-37d are drawings explaining a process of calculating a spatial position of a marker unit.

Figure 37A:
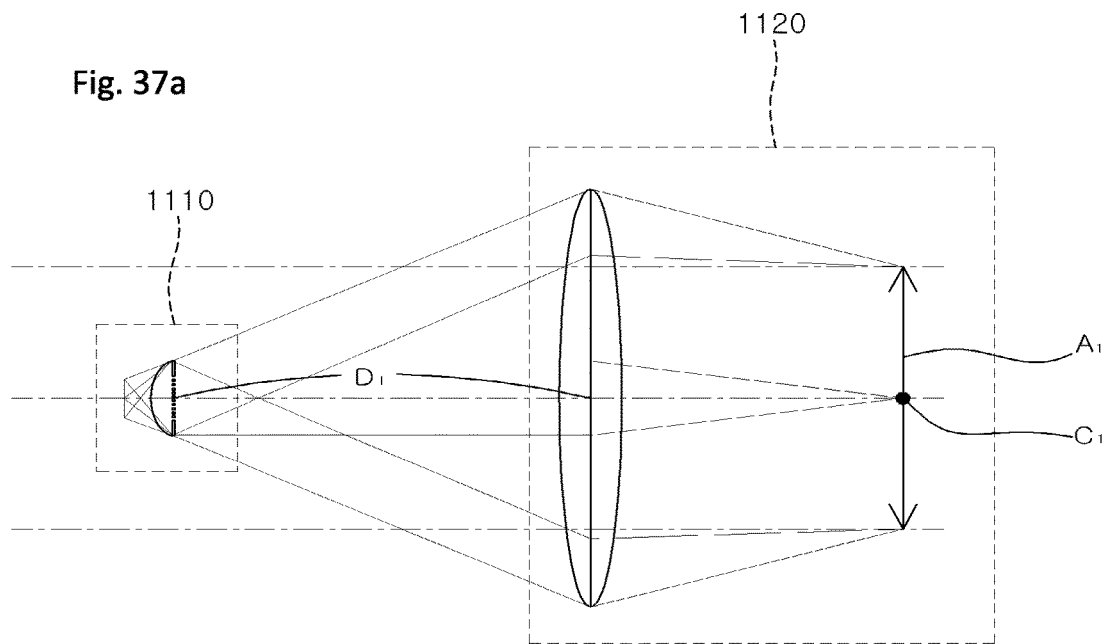
FIGS. 37a-37d are drawings explaining a process of calculating a spatial position of a marker unit.
Figure 37B:
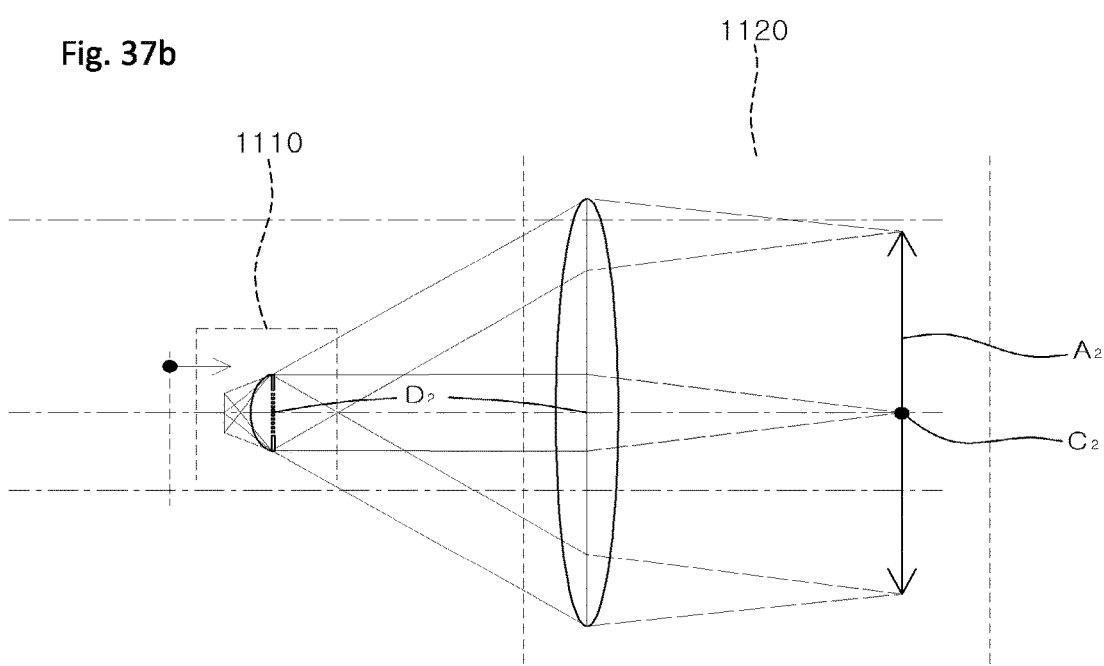
Figure 37C:
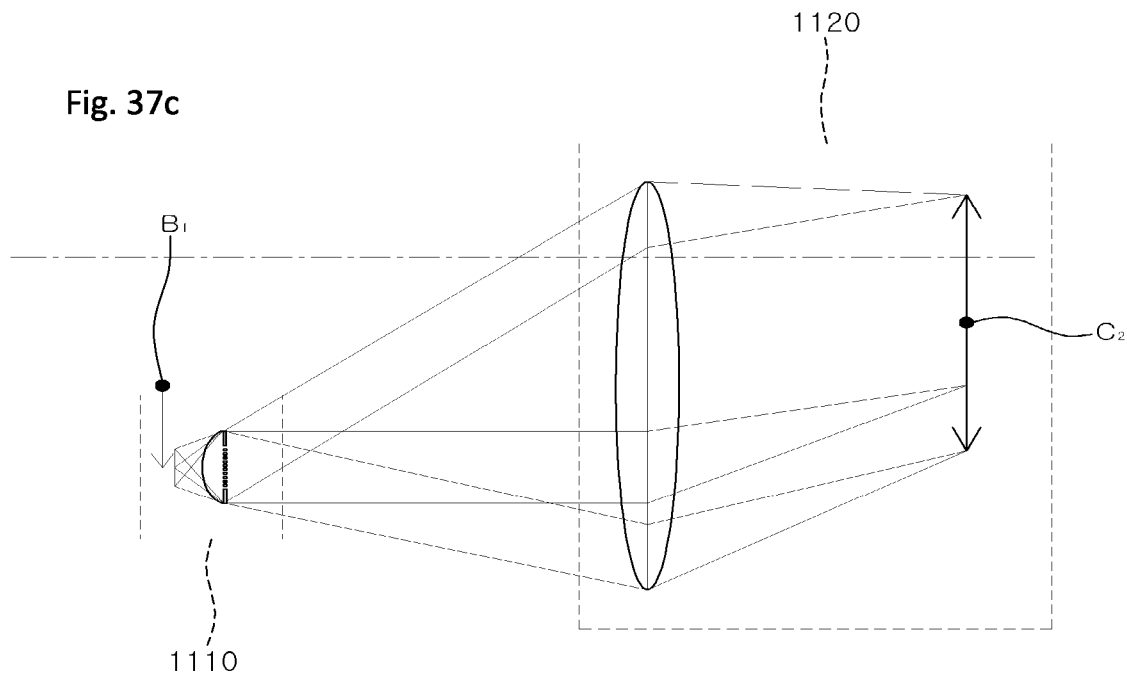
Figure 37D:
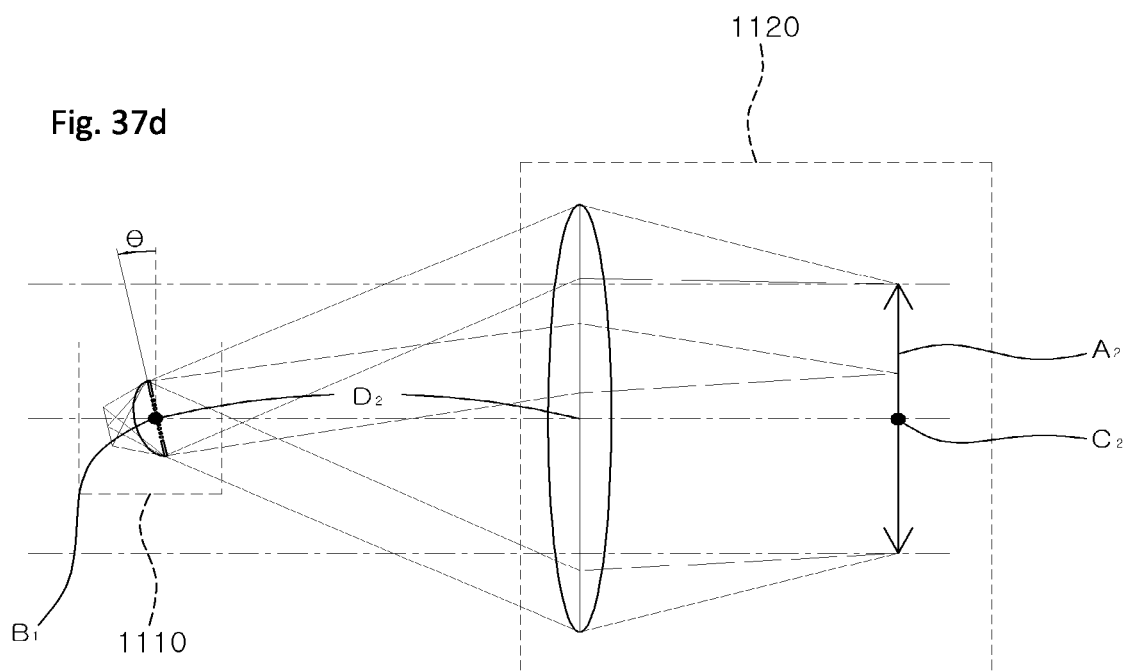

Referring to FIGS. 36-37d, in order to calculated the spatial position of the marker unit 1110, first, a position and a size change of the enlarged image of the pattern portion 1111 are measured (S3520).

After measuring the position and the size change of the enlarged image of the pattern portion 1111, the spatial position of the marker unit 1110 is calculated through the processor 1130 by comparing the position and the size change of the enlarged image of the pattern portion 1111 formed on the image forming unit 1120 with a reference position and a reference size of the image of the pattern portion 1111 which are pre-stored in the processor 1130 (S3521).

FIG. 37a shows the reference position and the size of the image of the pattern portion 1111 formed on the image forming unit 1120 when the marker unit 1110 is positioned on the pre-stored position, and as shown in FIG. 317b, when a distance D2 between the marker unit 110 and the image forming unit 1120 is shorter than a reference distance D1, then, a size A2 of the enlarged image of the pattern portion 1111 formed on the image forming unit 1120 is bigger than a reference size A1 of the image of the pattern portion 1111 which is pre-stored in the processor 1130. Therefore, the spatial position of the marker unit 1110 is calculated by comparing the reference size A1 of the image of the pattern portion 1111 with the size A2 of the enlarged image of the pattern portion formed on the image forming unit 1120.

Meanwhile, although it is not shown in the figure, when the distance D2 between the marker unit 1110 and the image forming unit 1120 is longer than the reference distance D1, then, the size A2 of the enlarged image of the pattern portion 1111 formed on the image forming unit 1120 is smaller than the reference size A1 of the image of the pattern portion 1111 which is pre-stored in the processor 1130.

And, when the marker unit 1110 is positioned below a reference position B1 as shown in FIG. 37c, the enlarged image of the pattern image of the pattern portion 1111 is formed on the image forming unit 1120 positioning above of a reference position C1 (Refer to FIG. 37a) of the image of the pattern portion 1111 which is pre-stored in the processor 1130. Therefore, the spatial position of the marker unit 1110 is calculated through the processor 1130 by comparing the reference position C1 of the image of the pattern portion 1111 with a position C2 of the enlarged image of the pattern portion 1111 formed on the image forming unit 1120.

Meanwhile, although it is not shown in the figure, when the marker unit 1110 is positioned at the reference position B1, the enlarged image of the pattern portion 1111 is formed on the image forming unit 120 positioning below of the reference position C1 of the image of the pattern portion 1111 which is pre-stored in the processor 1130.

And, when the distance D2 between the marker unit 1110 and the image forming unit 1120 is different to the reference distance D1 and the marker unit 110 is not positioned at the reference position B1, the spatial position of the marker unit 1110 is calculated by comparing the position C2 and the size A2 of the enlarged image formed on the image forming unit 1120 with the reference position C1 and the reference size A1 of the image of the pattern portion 1111 which is pre-stored in the processor 1130.

Meanwhile, as shown in FIG. 37d, when the distance D2 between the marker unit 1110 and the image forming unit 1120 is identical to the reference distance D1, the marker unit 1110 is positioned at the reference position B1 and the direction of the maker unit 1110 is changed as θ, the calculated size A2 and position C2 of the enlarged image of the pattern portion 1111 formed on the image forming unit 1120 are identical to the reference position C1 and the reference size A1 of the image of the pattern portion 111 which is pre-stored in the processor 1310. Therefore, the direction of the marker unit 1111 is calculated by calculating the rotated angle of the marker unit 1111 by comparing the position for each pattern portion 1111 and the size change of the pattern portion 1111 of the enlarged image $I_1$ of the pattern portion 1111 with the reference position for each pattern portion 1111 and the reference size of the pattern portion 1111 of the image $I_2$ of the pattern portion 111 which are pre-stored in the processor 1130.

As described above, an optical tracking system according to an embodiment of the present invention emits a parallel light of a pattern portion 1111 from a marker unit 1110, forms an enlarged image of the pattern portion 1111 on an image forming unit 1120, and calculates a spatial position of the marker unit 1110 using the enlarged image of the pattern portion 1111. In other words, the spatial position and the direction of a target to be calculated are calculated without reducing accuracy by enlarging an image of the pattern portion 1111 and forming the image on the image forming unit 1120, and therefore, an accuracy of the position of the marker unit is not dependent to a resolving power.

Therefore, an optical tracking system and a method using the same according to an embodiment of the present invention has an effect of expanding an available area by detecting an exact spatial position and a direction of a target regardless of a distance of the target to be calculated, as well as, a system downsizing is also capable compared with conventional system by reducing size of a marker unit 1110.

Meanwhile, the present invention has advantage of tracking more precisely a spatial position and a direction of a target since an angle of view and a resolution of an enlarged image of an pattern portion 1111 formed on the image forming unit 1120 are adjusted by adjusting a light quantity of a light which is emitted from a light source 1140 and incident on a mirror portion 1113 of a marker unit 1110.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

The invention claimed is:

1. An optical tracking system comprising:
   at least one marker configured to be attached to a target, the at least one marker including therein:
      at least one light source configured to irradiate light;
      at least one pattern portion formed by a plurality of patterns and arranged to receive the light irradiated by the at least one light source, the received light passing the at least one pattern portion or being reflected by the at least one pattern portion;
      a first lens arranged to receive the light, which has passed the at least one pattern portion or has been reflected by the at least one pattern portion, and configured to release a plurality of portions of the light, each released portion of the light having passed a specific point of the at least one pattern portion;
   at least one camera including:
      a second lens configured to receive and focus the light released from the first lens; and
      an image sensor configured to form an image of the at least one pattern portion based on the focused light; and
   a processor configured to calculate a spatial position and a direction of the at least one marker by using the image of the at least one pattern portion.

2. The optical tracking system of claim 1, wherein the processor is configured to calculate the spatial position of the at least one marker by using a position and a size of the image of the at least one pattern portion, and to calculate the direction of the at least one marker by using a position and a size change of the at least one pattern portion for each area of the image of the at least one pattern portion.

3. The optical tracking system of claim 2, wherein the processor is configured to:
   calculate the spatial position of the at least one marker by comparing the position and the size of the image of the at least one pattern portion with a pre-stored reference position and a pre-stored reference size of an image of the at least one pattern portion; and
   calculate the direction of the at least one marker by comparing the position and the size change of the at least one pattern portion for each area of the image of the at least one pattern portion with a pre-stored reference position and a pre-stored reference size change of the at least one pattern portion for each area of the image of the at least one pattern portion.

4. The optical tracking system of claim 1, wherein the first lens comprises a fish-eye lens.

5. The optical tracking system of claim 1, wherein the at least one marker further comprises a prism arranged to receive the light released from the first lens and configured to release the light to have a different angle of view.

6. A tracking method comprising:
   by at least one light source included in at least one marker of an optical tracking system, irradiating light to at least one pattern portion included in the at least one marker, the at least one pattern portion formed by a plurality of patterns and arranged to receive the light irradiated by the at least one light source, the received light passing the at least one pattern portion or being reflected by the at least one pattern portion;
   by a first lens included in the at least one marker, the first lens arranged to receive the light, which has passed the at least one pattern portion or has been reflected by the at least one pattern portion, releasing a plurality of portions of the light, each released portion of the light having passed a specific point of the at least one pattern portion;
   by a second lens included in at least one camera of the optical tracking system, receiving and focusing the light released from the first lens;
   by an image sensor included in the at least one camera, forming an image of the at least one pattern portion based on the focused light; and
   by a processor of the optical tracking system, calculating a spatial position and a direction of the at least one marker by using the image of the at least one pattern portion.

7. The tracking method of claim 6, wherein calculating the spatial position and the direction of the at least one marker comprises:
   calculating the direction of the at least one marker by calculating a rotated angle of the at least one marker by using the image of the at least one pattern portion; and calculating the spatial position of the at least one marker by using the image of the at least one pattern portion and the rotated angle of the at least one marker.

8. The tracking method of claim 7, wherein calculating the direction of the at least one marker comprises:

measuring a position and a size change of the at least one pattern portion for each area of the image of the at least one pattern portion; and calculating the rotated angle of the at least one marker by comparing a reference position and a reference size change of the at least one pattern portion for each area of an image of the at least one pattern portion, which are pre-stored in the processor, with the position and the size change of the at least one pattern portion for each area of the image of the at least one pattern portion.

9. The tracking method of claim 7, wherein calculating the spatial position of the at least one marker comprises:

measuring a position and a size of the image of the at least one pattern portion; and calculating the spatial position of the at least one marker by comparing a reference position and a reference size of an image of the at least one pattern portion which are pre-stored in the processor with the position and the size of the image of the at least one pattern portion.

10. The tracking method of claim 6, wherein the first lens comprises a fish-eye lens.

11. The tracking method of claim 6, wherein the at least one marker further comprises a prism arranged to receive the light released from the first lens and configured to release the light to have a different angle of view.

* * * * *